(12) United States Patent
Takasugi et al.

(10) Patent No.: US 8,690,765 B2
(45) Date of Patent: Apr. 8, 2014

(54) ENDOSCOPE APPARATUS AND IMAGE PROCESSING APPARATUS

(75) Inventors: Kei Takasugi, Hino (JP); Kazuma Kaneko, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1658 days.

(21) Appl. No.: 11/916,631

(22) PCT Filed: Jun. 5, 2006

(86) PCT No.: PCT/JP2006/311245
§ 371 (c)(1),
(2), (4) Date: Dec. 5, 2007

(87) PCT Pub. No.: WO2006/132191
PCT Pub. Date: Dec. 14, 2006

(65) Prior Publication Data
US 2009/0118578 A1    May 7, 2009

(30) Foreign Application Priority Data

Jun. 8, 2005  (JP) ................................. 2005-168614
Jul. 5, 2005  (JP) ................................. 2005-196713
Nov. 24, 2005  (JP) ................................. 2005-339317

(51) Int. Cl.
*A61B 1/06*  (2006.01)
(52) U.S. Cl.
USPC ........... 600/160; 600/109; 600/181; 600/178; 362/574
(58) Field of Classification Search
USPC ......... 600/108, 177–182, 111–112, 160, 166, 600/109; 362/84, 574
See application file for complete search history.

(56) References Cited

U.S. PATENT DOCUMENTS 4,821,117 A * 4/1989 Sekiguchi ....................... 348/68
(Continued)

FOREIGN PATENT DOCUMENTS

EP  1 161 919 A2  12/2001
(Continued)

OTHER PUBLICATIONS

Wagnieres et al., "An endoscopic fluorescence imaging system for simultaneous visual examination and photodetection of cancers", Review of Scientific Instruments AIP USA, vol. 68, No. 1, Jan. 1997, pp. 203-212, XP002552830.
(Continued)

*Primary Examiner* — John P Leubecker
*Assistant Examiner* — Arnaldo Torres Diaz
(74) *Attorney, Agent, or Firm* — Scully, Scott, Murphy & Presser, P.C.

(57) ABSTRACT

A normal light CCD 11 is driven via a normal light CCD control section 25 by a timing signal from a timing circuit section 29 of a video processor 20. At the same time, a fluorescence CCD 12 is driven via a fluorescence CCD control section 26. Then, an image pickup signal according to an RGB frame sequential method from the normal light CCD 11 is processed by a normal light image video circuit section 27 and a normal color image is created while an image pickup signal from the fluorescence CCD 12 is processed by a fluorescence image video circuit section 28, and an image pickup signal of a subject excited by blue illumination light and transmitted through a fluorescence transmitting filter 13 is extracted to create a fluorescence image of the subject. The normal color image and the fluorescence image of the subject are synthesized by an image synthesizing circuit section 30 and outputted to a monitor 2, whereby the normal light image and the fluorescence image is displayed side by side or on top of each other.

4 Claims, 29 Drawing Sheets

(56) References Cited

U.S. PATENT DOCUMENTS

| | | | |
|---|---|---|---|
| 5,412,705 A * | 5/1995 | Snoeren et al. | 378/98.3 |
| 6,602,186 B1 * | 8/2003 | Sugimoto et al. | 600/126 |
| 7,170,677 B1 * | 1/2007 | Bendall et al. | 359/464 |
| 7,179,222 B2 * | 2/2007 | Imaizumi et al. | 600/109 |
| 7,235,045 B2 * | 6/2007 | Wang et al. | 600/109 |
| 7,330,205 B2 * | 2/2008 | Hakamata | 348/65 |
| 7,341,557 B2 * | 3/2008 | Cline et al. | 600/160 |
| 2002/0062061 A1 | 5/2002 | Kaneko et al. | |
| 2002/0105505 A1 | 8/2002 | Sendai | |
| 2002/0175993 A1 | 11/2002 | Ueno et al. | |
| 2002/0177751 A1 | 11/2002 | Ueno et al. | |
| 2003/0135092 A1 | 7/2003 | Cline et al. | |
| 2004/0046865 A1 | 3/2004 | Ueno et al. | |
| 2004/0124791 A1 * | 7/2004 | Takahashi | 315/297 |
| 2004/0186351 A1 * | 9/2004 | Imaizumi et al. | 600/160 |
| 2004/0215060 A1 | 10/2004 | Ueno et al. | |
| 2004/0225222 A1 | 11/2004 | Zeng et al. | |
| 2005/0065406 A1 * | 3/2005 | Cline et al. | 600/160 |
| 2006/0149133 A1 * | 7/2006 | Sugimoto et al. | 600/160 |
| 2006/0235277 A1 * | 10/2006 | Ohkubo et al. | 600/179 |
| 2007/0149858 A1 * | 6/2007 | Ogawa et al. | 600/181 |
| 2008/0051632 A1 * | 2/2008 | Ito et al. | 600/114 |
| 2008/0089089 A1 * | 4/2008 | Hama et al. | 362/574 |
| 2009/0040598 A1 * | 2/2009 | Ito | 359/332 |

FOREIGN PATENT DOCUMENTS

| | | |
|---|---|---|
| EP | 1 258 220 | 11/2002 |
| EP | 1 258 221 A2 | 11/2002 |
| JP | 4-150845 | 5/1992 |
| JP | 09-066023 | 3/1997 |
| JP | 11-332819 | 12/1999 |
| JP | 2002-172082 | 6/2002 |
| JP | 2002-336196 | 11/2002 |
| JP | 2005-013611 | 1/2005 |
| JP | 2005-124756 | 5/2005 |
| WO | WO 2005/034747 A1 | 4/2005 |

OTHER PUBLICATIONS

Extended Supplementary European Search Report dated Nov. 10, 2009.

* cited by examiner

FIG.40
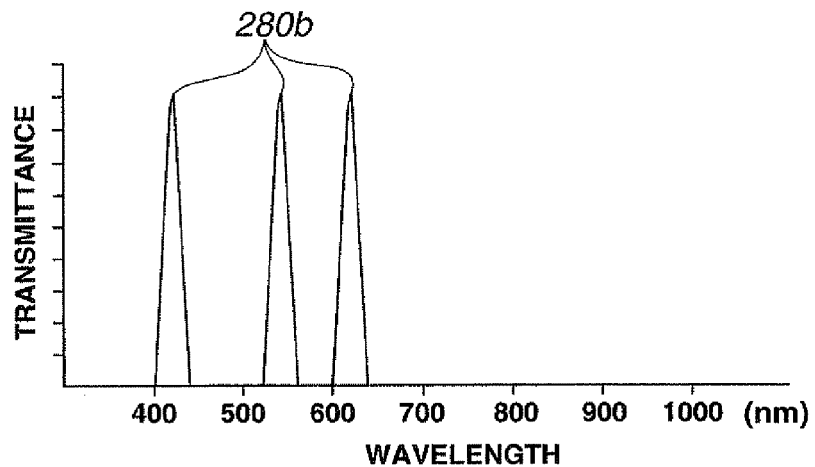
FIG.41
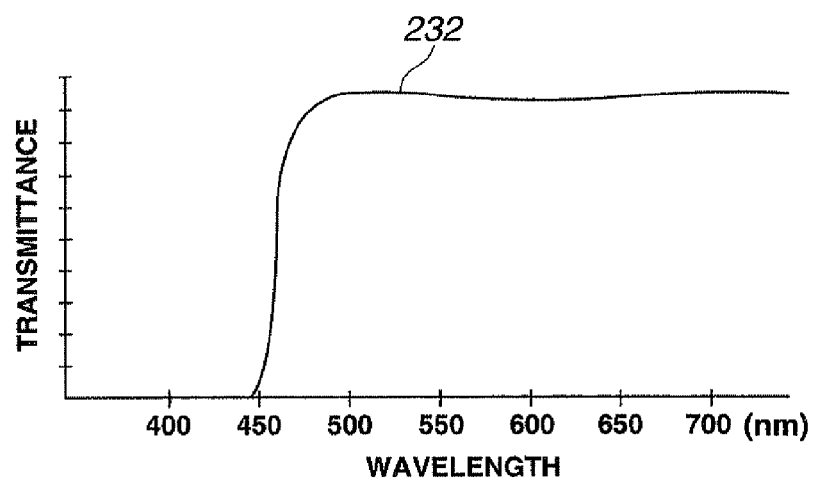
FIG.42
| MENU 1/2 | |
|---|---|
| DISPLAY SIZE | : FULL HEIGHT |
| FLUORESCENCE OBSERVATION DISPLAY SIZE | : MEDIUM |
| AREA OF INTEREST | : LARGE |
| IHb RANGE | : NORMAL |
| IHb AVERAGE | : ON |

FIG.46

| NUMBER IN TIME SERIES | 1 | 2 | 3 | 4 | 5-10 | 11 | 12 | 13 | 14 | 15 | 16 | 17 | 18 | 19 | 20 | 21 |
|---|---|---|---|---|---|---|---|---|---|---|---|---|---|---|---|---|
| CCD | 1 | 1 | 1 | 1 | 2 | 2 | 2 | 2 | 2 | 2 | 2 | 2 | 2 | 2 | 2 | 2 |
| ROTARY FILTER | B0 | R1 | G1 | B1 | X | R2 | R2 | G2 | G2 | B2 | B2 | R3 | R3 | G3 | G3 | B3 |
| WRITE INTO MEMORY SECTION | B0 | R1 | G1 | B1 | R2··· | - | R2 | - | G2 | - | B2 | - | R3 | - | G3 | - |
| READ FROM R MEMORY | R0 | - | R1 | R1 | - | R1' | - | R2 | R2 | R2 | R2 | R2 | R3 | R3 | - | - |
| READ FROM G MEMORY | G0 | - | - | G1 | G1··· | G1' | G1' | G1' | - | G2 | G2 | G2 | G2 | - | - | - |
| READ FROM B MEMORY | - | B0 | B0 | - | B1··· | B1' | B1' | B1' | B1' | B1' | - | B2 | B2 | B2 | B2 | B2 |
| OCCURRENCE OF NOISE (Δ) |  |  |  |  | Δ |  |  |  |  |  |  |  |  |  |  |  |
| MOVING IMAGE/STILL IMAGE | MOVING | MOVING | MOVING | STILL | STILL | MOVING | MOVING | MOVING | MOVING | MOVING | MOVING | MOVING | MOVING | MOVING | MOVING | MOVING |
| FREEZE INSTRUCTION |  |  |  |  |  | F1 |  |  |  |  |  |  |  |  |  | F2 |

FIG.47

MENU 2/2

FREEZE LEVEL : 4

COLOR SHIFT DETECTION : PRE-FREEZE

CHARACTER DISPLAY : FULL

PHOTOMETRY : AVERAGE

FIG.50

| NUMBER IN TIME SERIES | 1 | 2 | 3 | 4 | 5-10 | 11 | 12 | 13 | 14 | 15 | 16 | 17 |
|---|---|---|---|---|---|---|---|---|---|---|---|---|
| CCD | 1 | 1 | 1 | 1 | 2 | 2 | 2 | 2 | 2 | 2 | 2 | 2 |
| ROTARY FILTER | R1 | G1 | B1 | - | X | R8 | R8 | G8 | G8 | B8 | B8 | R9 |
| WRITE INTO SYNCHRONIZING CIRCUIT R | R1 | - | - | - | - | R8 | R8 | - | - | - | - | R9 |
| WRITE INTO SYNCHRONIZING CIRCUIT G | - | G1 | - | - | - | - | - | G8 | G8 | - | - | - |
| WRITE INTO SYNCHRONIZING CIRCUIT B | - | - | B1 | - | - | - | - | - | - | B8 | B8 | - |
| READ FROM SYNCHRONIZING CIRCUIT R | | R1 | R1 | R1 | R1 | - | - | R8 | R8 | R8 | R8 | - |
| READ FROM SYNCHRONIZING CIRCUIT G | G0 | - | G1 | G1 | G1 | G7 | G7 | - | - | G8 | G8 | G8 |
| READ FROM SYNCHRONIZING CIRCUIT B | B0 | B0 | - | B1 | B1 | B7 | B7 | B7 | B7 | - | - | B8 |
| DISPLAY R | R1 | R1 | R1 | R1 | R1 | R8 | R8 | R8 | R8 | R8 | R8 | R9 |
| DISPLAY G | G0 | G1 | G1 | G1 | G1 | G7 | G7 | G8 | G8 | G8 | G8 | G8 |
| DISPLAY B | B0 | B0 | B1 | B1 | B1 | B7 | B7 | B7 | B7 | B8 | B8 | B8 |
| MOVING IMAGE/STILL IMAGE | MOVING | MOVING | MOVING | STILL | STILL | MOVING | MOVING | MOVING | MOVING | MOVING | MOVING | MOVING |

ENDOSCOPE APPARATUS AND IMAGE PROCESSING APPARATUS

TECHNICAL FIELD

The present invention relates to an endoscope apparatus and an image processing apparatus capable of obtaining observation images under normal light and observation images under fluorescence.

BACKGROUND ART

Observation of living tissue by an endoscope includes, in addition to normal endoscopic observation using visible light, fluorescence observation in which fluorescence pictures are observed by irradiating excitation light. The fluorescence observation utilizes a characteristic in which, when light (excitation light) whose wavelength falls within 400 nm to 480 nm is irradiated to living tissue, normal tissue intensely emits fluorescence in the range of approximately 480 nm to 630 nm while fluorescence from diseased parts such as carcinoma cells is weaker, and is known as a technique that enables discovery of abnormal regions such as early cancer that are difficult to view under normal endoscopic observation.

Conventionally, as disclosed in Japanese Patent Laid-Open No. 4-150845, in an endoscope apparatus used in fluorescence observation, an excitation filter that transmits only excitation light is positioned in a path of illumination light emitted from a light source, and at the same time, a fluorescence transmitting filter that transmits only light having a fluorescence wavelength is positioned between an objective optical system at a distal end of an insertion portion of the endoscope and a solid state image pickup device.

With a conventional apparatus such as that disclosed in Japanese Patent Laid-Open No. 4-150845, illumination light irradiating a subject is limited to excitation light and light beams incident to the solid state image pickup device is limited to fluorescence. Consequently, the conventional apparatus becomes an apparatus dedicated to fluorescence observation which is incapable of performing endoscopic observation on the subject under normal light.

Therefore, conventionally, every time an endoscopic observation is performed in order to visually observe positions or conditions of a diseased part, it is required that an endoscope apparatus for fluorescence observation be replaced with an endoscope apparatus for normal light observation and vice versa for alternate use, thereby placing a heavy burden on both patients and doctors.

In consideration thereof for example, in Japanese Patent Laid-Open No. 9-066023, a video processor apparatus involving an electronic endoscope for fluorescence observation is proposed which is capable of readily performing both normal endoscopic observation and fluorescence observation. However, with such an apparatus, although both a normal light observation image and a fluorescence observation image are displayable on a monitor, a normal light observation image and a fluorescence observation image picked up at the same timing cannot be observed simultaneously. This creates a problem in that it is difficult to compare a normal light observation image and a fluorescence observation image, such as, for example, the same region cannot be observed when a subject moves during switching of observation images.

In addition, another problem exists in that, when displaying both a normal light observation image and a fluorescence observation image on the monitor, a state in which one of the images changes to a noise image or a state in which nothing is outputted occurs in the event that either a normal light observation CCD or a fluorescence observation CCD has a trouble, making it difficult to recognize on the monitor screen which CCD has a trouble.

Moreover, in addition to normal observation and fluorescence observation described above, observation of living tissue using an endoscope apparatus includes Narrow Band Imaging (NBI) in which narrowband light that is light whose band is narrower than that of illumination light used in normal observation is irradiated in vivo to perform observation, and infrared observation in which near-infrared light that is light having a near-infrared band is irradiated in vivo to perform observation.

Narrow Band Imaging enables observation of vessels in a superficial portion of mucous membrane at a higher contrast, while infrared observation enables observation of hemodynamics in submucous deep regions not viewable through normal observation by intravascular injection of an agent called indocyanine green (ICG) which absorbs near-infrared light.

Such an apparatus that enables switching among a plurality of observation modes is disclosed in, for example, Japanese Patent Laid-Open No. 2005-013611 as an image processing apparatus capable of switching among four observation modes, namely, normal observation, fluorescence observation, Narrow Band Imaging and infrared observation.

However, with fluorescence observation, since autofluorescence emitted by living tissue in vivo is weak, pickup of pictures under autofluorescence emitted by living tissue in vivo is performed by, for example, reducing the rotation speed of a rotary filter provided at a light source in comparison to normal observation in order to extend exposure time in comparison to normal observation.

Therefore, for example, during a time period in which the observation mode of an endoscope apparatus switches from normal observation to fluorescence observation or, in other words, during a time period in which the rotation speed of the rotary filter changes from a rotation speed suitable for normal observation to a rotation speed suitable for fluorescence observation, a problem arises in that a still image unsuitable for storing is outputted. Such a problem is not considered in Japanese Patent Laid-Open No. 2005-013611.

The present invention has been made in consideration of the above circumstances, and has as its object to provide an endoscope apparatus capable of readily comparing an normal light observation image and a fluorescence observation image and notifying an malfunction in an image processing system on the monitor, and to provide an image processing apparatus capable of outputting a still image suitable for storing when switching among observation modes is being performed.

DISCLOSURE OF INVENTION

Means for Solving the Problem

In order to achieve the above object, an endoscope apparatus according to a first aspect of the present invention comprises: an endoscope including normal light image pickup means having an electronic shutter and which picks up a subject picture under normal light and fluorescence image pickup means that picks up a fluorescence picture from a subject; and an image processing apparatus that performs signal processing on image pickup signals from the normal light image pickup means and the fluorescence image pickup means to create a normal light image and a fluorescence image, wherein the image processing apparatus includes: normal light image pickup control means that drives the normal light image pickup means; fluorescence image pickup control means that drives the fluorescence image pickup means; normal light image signal processing means that performs signal processing on an image pickup signal from the normal light image pickup means to create a normal light image; and fluorescence image signal processing means that performs signal processing on an image pickup signal including a fluorescence picture of the subject to create a fluorescence image, further wherein the normal light image pickup control means and the fluorescence image pickup control means are simultaneously driven.

An endoscope apparatus according to a second aspect of the present invention comprises: an endoscope including normal light image pickup means that picks up a subject picture under normal light and fluorescence image pickup means that picks up a fluorescence picture from a subject; and an image processing apparatus that performs signal processing on image pickup signals from the normal light image pickup means and the fluorescence image pickup means to create a normal light image and a fluorescence image, wherein the image processing apparatus includes: normal light image pickup driving means that drives the normal light image pickup means; fluorescence image pickup driving means that drives the fluorescence image pickup means; normal light image signal processing means that performs signal processing on an image pickup signal from the normal light image pickup means to create a normal light image; fluorescence image signal processing means that performs signal processing on an image pickup signal including the fluorescence picture to create a fluorescence image; image synthesizing means that synthesizes the normal light image and the fluorescence image; normal light image processing monitoring means that monitors the normal light image signal processing system from a driving signal of the normal light image pickup driving means to an output signal of the normal light image signal processing means; and fluorescence image processing monitoring means that monitors the fluorescence image signal processing system from a driving signal of the fluorescence image pickup driving means to an output signal of the fluorescence image signal processing means.

An image processing apparatus according to a third aspect of the present invention comprises: image pickup means that performs image pickup on a subject and outputs an image pickup signal based on the picked up subject picture; one or more storing means that stores an image pickup signal outputted from the image pickup means; write signal generating means that outputs to the storing means a write signal that causes the storing means to store the image pickup signal; switching signal generating means that outputs to the image pickup means and the storing means a switching signal for switching between a first observation mode that creates a first observation image based on an image pickup signal outputted from the image pickup means and a second observation mode that creates a second observation image that differs from the first observation signal based on an image pickup signal outputted from the image pickup means; write inhibiting means that causes writing of the image pickup signal to the storing means to be suspended by stopping output of the write signal based on the switching signal; and write inhibition releasing means that releases suspension of writing of the image pickup signal to the storing means by restarting output of the write signal to the storing means when a predetermined time has elapsed after output of the switching signal.

An image processing apparatus according to a fourth aspect of the present invention comprises: one or more image pickup means that performs image pickup on a subject and outputs an image pickup signal based on the picked up subject picture; one or more storing means that stores an image pickup signal outputted from the image pickup means; write signal generating means that outputs to the storing means a write signal that causes the storing means to store the image pickup signal; light source means that irradiates the subject with an illumination light having a first band and an illumination light having a second band that differs from the second illumination light; switching signal generating means that outputs to the image pickup means and the storing means a switching signal for switching between a first observation mode in which, when an illumination light having the first band is irradiated to the subject, image pickup on the subject over a first exposure time is performed and a second observation mode in which, when an illumination light having the second band is irradiated to the subject, image pickup on the subject over a second exposure time is performed; write inhibiting means that causes writing of the image pickup signal to the storing means to be suspended by stopping output of the write signal based on the switching signal; and write inhibition releasing means that releases suspension of writing of the image pickup signal to the storing means by restarting output of the write signal to the storing means after output of the switching signal and after the illumination light irradiated by the light source means is switched from one illumination light to the other illumination light.

An image processing apparatus according to a fifth aspect of the present invention comprises: a plurality of image pickup means that performs image pickup on a subject and outputs an image pickup signal based on the picked up subject picture; one or more storing means that stores an image pickup signal outputted from the image pickup means; write signal generating means that outputs to the storing means a write signal that causes the storing means to store the image pickup signal; switching signal generating means that outputs a switching signal for switching between a first image pickup signal that is outputted from the image pickup means when the image pickup means picks up a first picture of the subject and a second image pickup signal that is outputted from the image pickup means when the image pickup means picks up a second picture of the subject which differs from the first picture; write inhibiting means that causes writing of the first image pickup signal or the second image pickup signal to the storing means to be suspended by stopping output of the write signal based on the switching signal; and write inhibition releasing means that releases suspension of writing of the first image pickup signal or the second image pickup signal to the storing means by restarting output of the write signal to the storing means after output of the switching signal and after the image pickup signal outputted from the image pickup means is switched from one image pickup signal to the other image pickup signal.

BRIEF DESCRIPTION OF THE DRAWINGS

FIG. 40 is a diagram showing transmission characteristics of a Narrow Band Imaging filter provided in the band switching filter shown in FIG. 38, according to the fifth embodiment of the present invention;

FIG. 41 is a diagram showing transmission characteristics of an excitation light cutoff filter provided in an electronic endoscope included in the endoscope apparatus according to the fifth embodiment of the present invention;

FIG. 42 is a diagram showing an example of a setting screen of a processor included in the endoscope apparatus according to the fifth embodiment of the present invention;

FIG. 46 is a diagram showing write and read states of image pickup signals to/from memory sections when the observation mode of the endoscope apparatus is switched from one observation mode to another observation mode according to the fifth embodiment of the present invention;

FIG. 47 is a diagram showing an example, which differs from that of FIG. 42, of the setting screen of the processor included in the endoscope apparatus according to the fifth embodiment of the present invention;

FIG. 50 is a diagram showing write and read states of image pickup signals at a synchronizing circuit when the observation mode of the endoscope apparatus is switched from one observation mode to another observation mode according to the fifth embodiment of the present invention.

BEST MODE FOR CARRYING OUT THE INVENTION

Embodiments of the present invention will now be described with reference to the drawings.

[First Embodiment]

Figure 1:
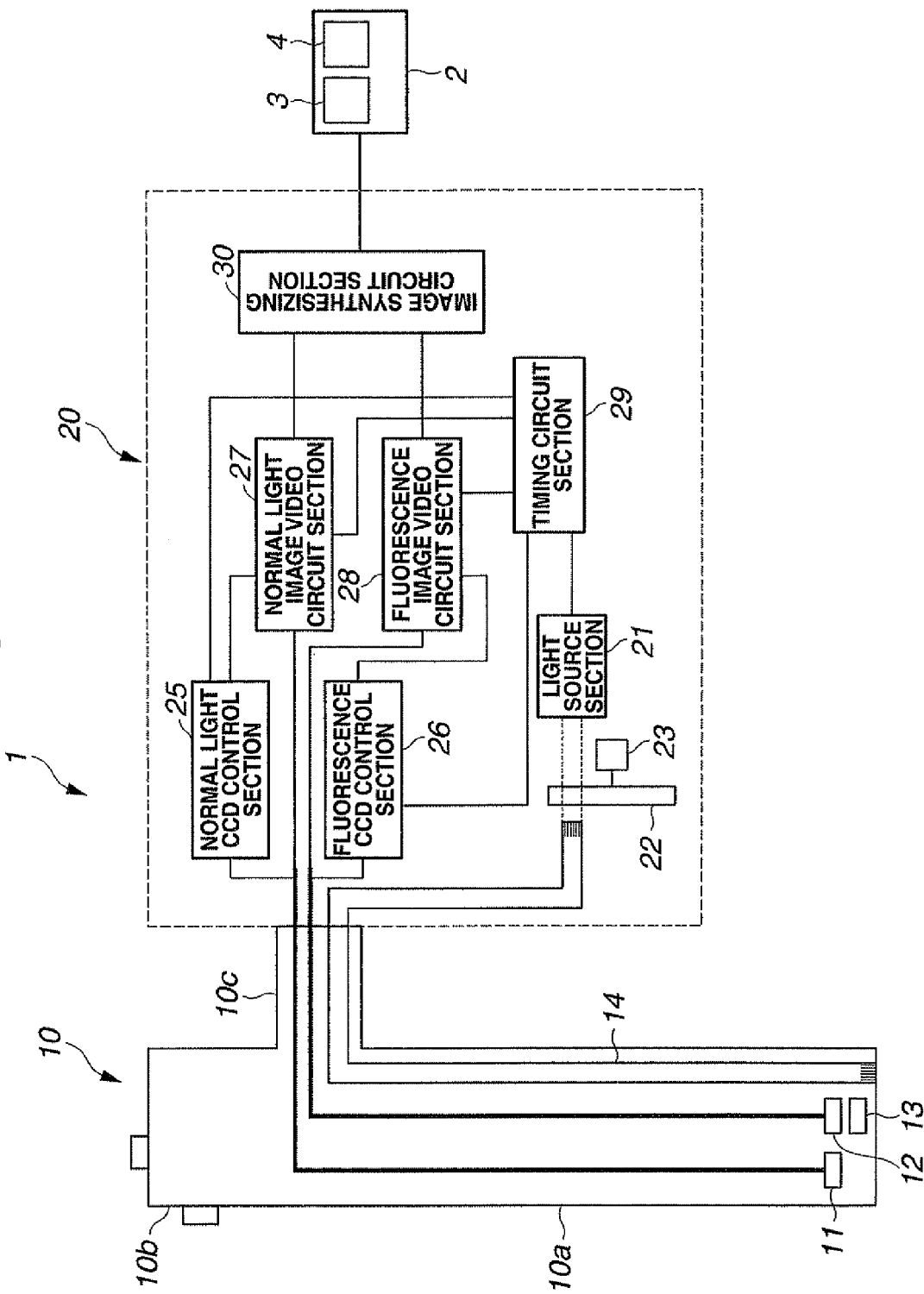
FIG. 1 is a block diagram showing a configuration of an endoscope apparatus according to a first embodiment of the present invention.

In FIG. 1, reference numeral 1 denotes an endoscope apparatus. The endoscope apparatus 1 comprises: an electronic endoscope 10 capable of normal light observation of a subject under visible light and fluorescence observation under fluorescence emitted by the subject; and a video processor 20 as an image processing apparatus that drives the electronic endoscope 10 and performs signal processing on a normal light observation picture and a fluorescence observation picture picked up by the electronic endoscope 10 to create a normal light image and a fluorescence image. A monitor 2 is connected to the video processor 20. A normal light observation image 3 and a fluorescence observation image 4 are displayed on a screen of the monitor 2.

The electronic endoscope 10 comprises a flexible insertion portion 10a to be inserted into a body cavity or the like and an operation section 10b provided at a proximal end side of the insertion portion 10a, and is connected to the video processor 20 via a universal cord 10c extended from a lateral portion of the operation section 10b. An image pickup device 11 that is normal light image pickup means and an image pickup device 12 that is fluorescence image pickup means are anteriorly oriented and positioned side by side at a distal end portion of the insertion portion 10a. For the image pickup device 11 for normal light image pickup, a solid state image pickup device supporting an electronic shutter function such as a monochromatic charge-coupled device (CCD) is used. For the image pickup device 12 for fluorescence image pickup, for example, a highly sensitive solid state image pickup device capable of capturing weak in vivo fluorescence is used.

Note that, hereinafter, the image pickup device 11 for normal light image pickup shall primarily be described as a normal light CCD 11 and the image pickup device 12 for fluorescence image pickup shall primarily be described as a fluorescence CCD 12.

In regards to the normal light CCD 11 and the fluorescence CCD 12, a fluorescence transmitting filter 13 that transmits only light whose wavelength is in the range of 520 nm to 700 nm is positioned at a front face of one of the CCDs, namely, the fluorescence CCD 12, and a fluorescence transmitting filter is not positioned in front of the other CCD, namely, the normal light CCD 11. An objective optical system (not shown) is positioned anteriorly to the CCDs 11 and 12, and a picture of an anterior subject is formed on image pickup planes of the respective CCDs 11 and 12.

A single common objective optical system may alternatively be arranged with respect to both the normal light CCD 11 and the fluorescence CCD 12.

In addition, an output end of an illumination light guide fiber bundle (hereinafter simply described as "light guide") 14 is positioned via an illumination optical system (not shown) alongside the objective optical system at the distal end of the insertion portion 10a. The light guide 14 is connected from the insertion portion 10a via the universal cord 10c to the video processor 20. The light guide 14 guides illumination light incident to an incident end from a light source provided in the video processor 20, and irradiates the illumination light from an output end at a distal end of the endoscope towards an observation range of the objective optical system.

The video processor 20 comprises a light source system for supplying illumination light to the light guide 14 as well as various signal processing circuit systems for driving the CCDs and performing signal processing. As the light source system for supplying illumination light, a light source section 21 that includes, for example, a xenon lamp and a modulated light circuit or the like is provided. An RGB rotary filter 22 is positioned in an illumination light path between the light source section 21 and the incident end of the light guide 14.

Figure 2:
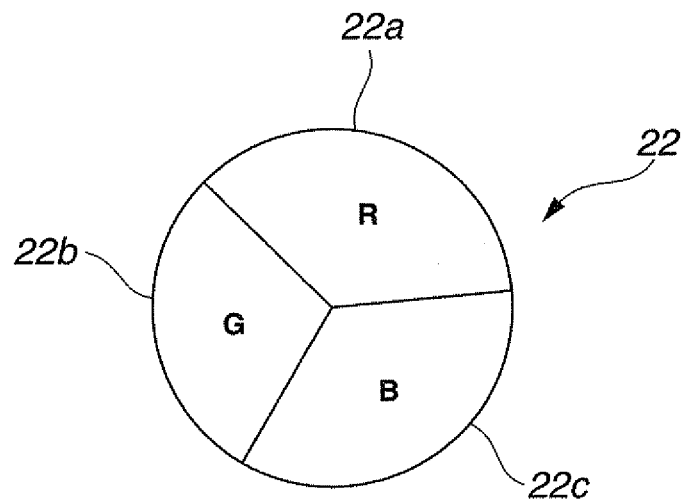
FIG. 2 is an explanatory diagram showing a configuration of an RGB rotary filter according to the first embodiment of the present invention.

Output light from the light source section 21 is transmitted through the RGB rotary filter 22 and guided by the light guide 14, and outputted from the distal end of the insertion portion 10a of the electronic endoscope 10. As shown in FIG. 2, the RGB rotary filter 22 is constituted by three filters 22a, 22b and 22c respectively colored red (R), green (G) and blue (B) and formed in a fan-like shape, and is rotated at a constant speed by a motor 23 that is controlled via the light source section 21. Consequently, a subject anterior to the distal end of the insertion portion 10a of the electronic endoscope 10 is sequentially and repetitively illuminated by illumination lights having the three colors of red, green and blue.

Incidentally, wavelength ranges of light transmitted by the respective filters 22a, 22b and 22c are, for example, red (R): 580 nm to 650 nm, green (G): 500 nm to 580 nm, and blue (B): 400 nm to 500 nm.

Furthermore, as the various signal processing circuit systems of the video processor 20, there are provided: a normal light CCD control section 25 as normal light image pickup control means that drives/controls the normal light CCD 11; a fluorescence CCD control section 26 as fluorescence image pickup control means that drives/controls the fluorescence CCD 12; a normal light image video circuit section 27 as normal light image signal processing means that processes an image pickup signal from the normal light CCD 11 and creates a normal light image; a fluorescence image video circuit section 28 as fluorescence image signal processing means that processes an image pickup signal from the fluorescence CCD 12 and creates a fluorescence image; a timing circuit section 29 that creates a timing signal for synchronizing and operating the respective sections; and an image synthesizing circuit section 30 that synthesizes a normal light image and a fluorescence image and outputs the same to the monitor 2.

The normal light CCD control section 25 drives the normal light CCD 11, and controls image pickup under an illumination light irradiated to the subject via the RGB rotary filter 22. In addition, when the volume of illumination light is increased to accommodate fluorescence observation, exposure control by an electronic shutter of the normal light CCD 11 is performed in order to adjust light exposure so that a normal light image having optimum brightness is obtained.

The fluorescence CCD control section 26 drives the fluorescence CCD 12, and controls image pickup of a subject picture that includes a picture under fluorescence emitted from the subject by illumination light irradiated to the subject via the RGB rotary filter 22. At this point, in the event that a fluorescence image having sufficient brightness cannot be obtained even when the light quantity of illumination light is maximized, adjustment is performed by controlling the gain of the fluorescence CCD 12 so that a fluorescence image having sufficient brightness can be obtained.

The normal light image video circuit section 27 processes an image pickup signal transferred from the normal light CCD 11 and creates a normal color video signal of the subject. On the other hand, the fluorescence image video circuit section 28 extracts an image pickup signal under a light whose wavelength is transmitted by the fluorescence transmitting filter 13 from image pickup signals transferred from the fluorescence CCD 12, and creates a fluorescence image of the subject.

The timing circuit section 29 creates a timing signal and supplies the same to the normal light CCD control section 25, the fluorescence CCD control section 26, the normal light image video circuit section 27, the fluorescence image video circuit section 28, and the light source section 21 that controls the motor 23 which rotates the RGB rotary filter 22. Based on the timing signal, the normal light CCD control section 25 and the fluorescence CCD control section 26 are simultaneously driven, enabling a subject picture under normal light and a fluorescence picture picked up at the same timing by the normal light CCD 11 and the fluorescence CCD 12 to be obtained. In addition, processing by the normal light image video circuit section 27 and the fluorescence image video circuit section 28, as well as the rotation of the RGB rotary filter 22 by the motor 23 are synchronized and controlled.

The image synthesizing circuit section 30 synthesizes an normal light image from the normal light image video circuit section 27 and a fluorescence image from the fluorescence image video circuit section 28, outputs a synthesized image constituted by either one of or both the normal light image and the fluorescence image, and causes the synthesized image to be displayed on the screen of the monitor 2. FIG. 1 shows an example in which the normal light observation image 3 and the fluorescence observation image 4 are displayed side by side.

In endoscopic observation by the endoscope apparatus 1 configured as described above, lamp emission of the light source section 21 and rotation of the RGB rotary filter by the motor 23 are controlled based on a timing signal from the timing circuit section 29 of the video processor 20, and the subject is sequentially and repetitively illuminated by illumination lights having the three colors of red, green and blue. Furthermore, based on the timing signal from the timing circuit section 29, the normal light CCD 11 is driven via the normal light CCD control section 25 and, at the same time, the fluorescence CCD 12 is driven via the fluorescence CCD control section 26.

As a result, at the normal light CCD 11, image pickup is performed under a so-called RGB frame sequential method. Accordingly, an image pickup signal under the RGB frame sequential method is inputted to the normal light image video circuit section 27. At the normal light image video circuit section 27, synchronization of the R, G and B signals is performed after noise reduction or color balance correction through preprocessing, and further, a normal color video signal of the subject is created by performing processing such as gamma correction and color correction.

Figure 3:
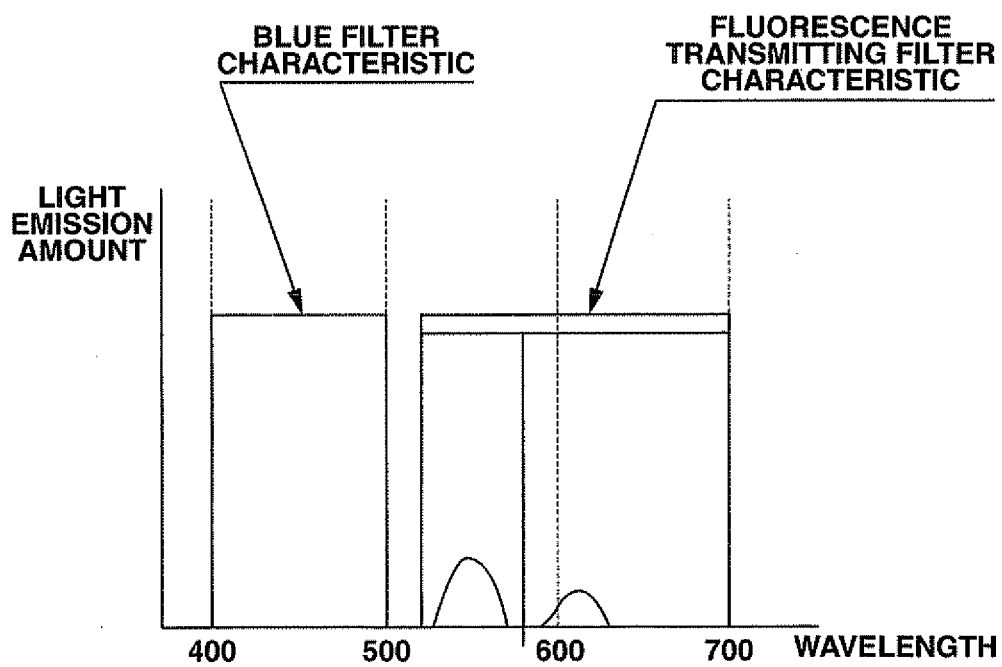
FIG. 3 is an explanatory diagram showing fluorescence wavelength bands and respective filter characteristics according to the first embodiment of the present invention.

On the other hand, an image pickup signal from the fluorescence CCD 12 is inputted to the fluorescence image video circuit section 28. At the fluorescence image video circuit section 28, only a signal at a time point where the subject is illuminated by the blue illumination light (wavelength: 400 nm to 500 nm) among the red, green and blue illumination lights from the RGB rotary filter 22 is extracted and a fluorescence image of the subject is created. In other words, an image to be obtained at the fluorescence CCD 12 is limited to a picture under light whose wavelength can be transmitted through the fluorescence transmitting filter 13. As shown in FIG. 3, light having a wavelength of 520 nm to 700 nm is excited from the subject by excitation light having a wavelength of 400 nm to 500 nm included in the blue illumination light, and a fluorescence image is created from a subject picture transmitted through the fluorescence transmitting filter 13 and picked up by the fluorescence CCD 12.

In this case, since fluorescence emitted in vivo is weak, it is necessary to increase the light quantity of the illumination light as compared to normal light observation in order to obtain a clear fluorescence image. However, with the electronic endoscope 10 according to the present embodiment, a common illumination light is shared by normal light observation and fluorescence observation. This may result in a case where an increase in illumination light quantity to accommodate fluorescence observation creates too bright illumination light for a normal light image and an optimum illumination light quantity is not obtained.

Therefore, the normal light CCD control section 25 performs electronic shutter control of the normal light CCD 11 and adjusts light exposure to ensure that a normal light image having optimum brightness is obtained. Well known general control shall suffice as a light exposure adjustment method using an electronic shutter, in which, with respect to illumination light that is too bright, control is exercised so that a charge accumulation time of the normal light CCD 11 is shortened while keeping a constant color balance between the respective colors of R, G and B, thereby adjusting the light quantity contributing towards image pickup or, in other words, the brightness of an image to an optimum light quantity.

Furthermore, in the event that sufficient brightness cannot be obtained even when maximizing illumination light quantity, the fluorescence CCD control section 26 ensures that a fluorescence image having optimum brightness is obtained by controlling the gain of the fluorescence CCD 12. For example, in a case where a high-sensitivity image pickup device provided with a charge multiplication mechanism that utilizes ionization of a CMD (Charge Multiplication Device) is used, the fluorescence CCD control section 26 compensates for deficiency in illumination light quantity and ensures that a fluorescence image having optimum brightness is obtained by controlling a control pulse or an applied voltage to the device in order to increase the gain of the signal within the device.

A color image created by the normal light image video circuit section 27 and a fluorescence image created by the fluorescence image video circuit section 28 are inputted to the image synthesizing circuit section 30 to be subjected to synthesis processing. As a result, a synthesized image constituted by either one of or both the fluorescence image and the normal light image is created. This synthesized image is outputted from the image synthesizing circuit section 30 to the monitor 2 and, for example, as shown in FIG. 1, the normal light observation image 3 and the fluorescence observation image 4 are displayed side by side on the screen of the monitor 2.

Incidentally, in FIG. 1, while the normal light observation image 3 and the fluorescence observation image 4 are displayed side by side, display methods are not limited to this arrangement. Instead, the normal light observation image 3 and the fluorescence observation image 4 may be superimposed and displayed.

As described above, with the endoscope apparatus 1 according to the present embodiment, since a normal light observation image and a fluorescence observation image can be obtained at the same time, the task of switching between normal light observation and fluorescence observation required heretofore is no longer necessary, thereby improving operability of the observer and reducing the burden placed thereon by switching operations. In addition, since it is now possible to view images under different observation modes obtained at the same timing, there is an advantage in that comparisons between a fluorescence observation image and a normal light observation image can be performed with greater ease, thereby contributing towards the improvement of diagnostic performance.

Furthermore, by performing exposure control of a normal light image pickup device or gain control of a fluorescence image pickup device, it is now possible to arrange both a normal light observation image and a fluorescence observation image as images with optimum brightness with respect to a common illumination light, thereby simplifying the configuration of the light source system and achieving reduction in system cost.

[Second Embodiment]

Next, a second embodiment of the present invention will be described. In contrast to the first embodiment described above, the second embodiment is provided with an illumination system that outputs blue excitation light for fluorescence observation which is a separate system to the illumination system for normal light observation. Note that members and circuit sections that perform like operations as the first embodiment are assigned like reference characters, and that descriptions thereof will be omitted.

Figure 4:
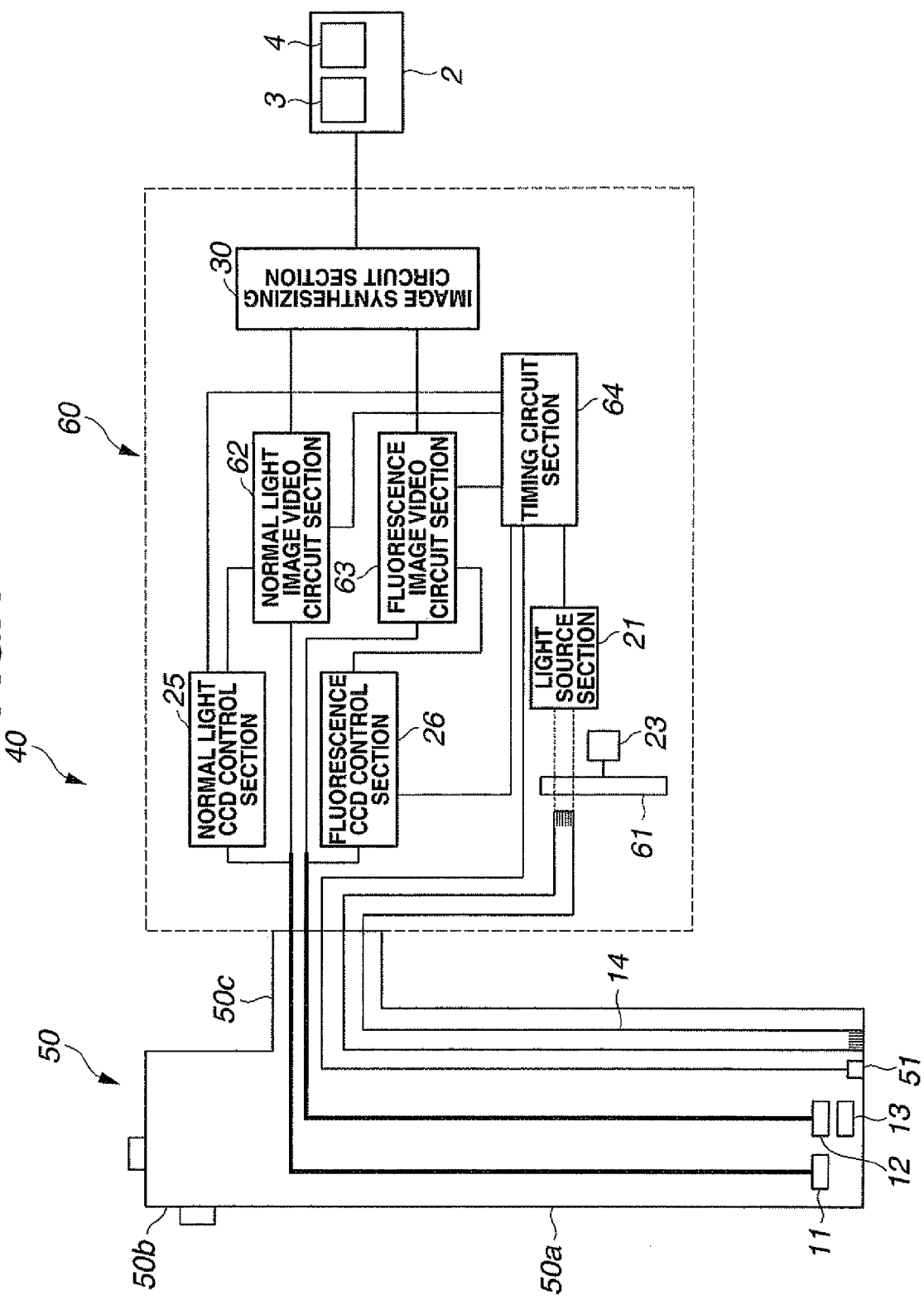
FIG. 4 is a block diagram showing a configuration of an endoscope apparatus according to a second embodiment of the present invention.

As shown in FIG. 4, an endoscope apparatus 40 according to the second embodiment comprises: an electronic endoscope 50 capable of normal light observation and fluorescence observation; and a video processor 60 that drives the electronic endoscope 50, performs signal processing on a normal light observation picture and a fluorescence observation picture from the electronic endoscope 50, and displays a normal light observation image and a fluorescence observation image on the monitor 2. In a similar manner to the electronic endoscope 10 of the first embodiment, the electronic endoscope 50 comprises a flexible insertion portion 50*a* and an operation section 50*b* provided at a proximal end side of the insertion portion 50*a*, and is connected to the video processor 60 via a universal cord 50*c* extended from a lateral portion of the operation section 50*b*.

A normal light CCD 11 and a fluorescence CCD 12 are anteriorly oriented and positioned side by side at a distal end portion of the insertion portion 50*a* of the electronic endoscope 50. A fluorescence transmitting filter 13 that transmits only light whose wavelength is in the range of 520 nm to 700 nm is positioned at a front face of one of the CCDs, namely, the fluorescence CCD 12, and a fluorescence transmitting filter is not positioned anterior to the other CCD, namely, the normal light CCD 11. In addition, positioned alongside an output end of a light guide 14 that irradiates illumination light towards an observation range of an objective optical system of both CCDs 11 and 12 is a blue LED 51 for outputting blue excitation light as illumination light from a light path of a system separate from the light guide 14.

Compared to the video processor 20 according to the first embodiment, while the video processor 60 corresponding to the electronic endoscope 50 similarly comprises: a normal light CCD control section 25 that drives/controls the normal light CCD 11; a fluorescence CCD control section 26 that drives/controls the fluorescence CCD 12; and an image synthesizing circuit section 30 that synthesizes a normal light image and a fluorescence image and outputs the same to the monitor 2, there are slight differences in the functional configurations of: an RGB rotary filter 61 positioned in an illumination light path between a light source section 21 and an incident end of the light guide 14; a normal light image video circuit section 62 that processes an image pickup signal from the normal light CCD 11 and creates a normal light image; a fluorescence image video circuit section 63 that processes an image pickup signal from the fluorescence CCD 12 and creates a fluorescence image; and a timing circuit section 64 that creates a timing signal for synchronizing and operating the respective sections.

Figure 5:
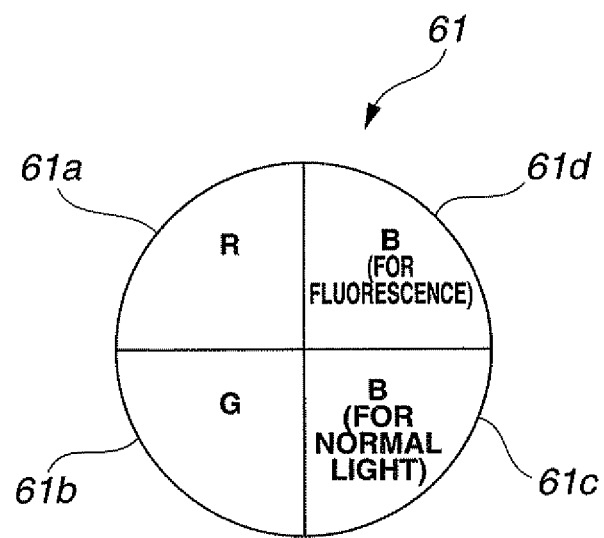
FIG. 5 is an explanatory diagram showing a configuration of an RGB rotary filter according to the second embodiment of the present invention.

As shown in FIG. 5, in addition to three filters 61*a*, 61*b* and 61*c* for normal light observation which are respectively colored red (R), green (G) and blue (B), the RGB rotary filter 61 is provided with a blue filter 61*d* for fluorescence observation adjacent to the blue filter 61*c* and the red filter 61*a* for normal light observation. The respective filters are formed in fan-like shapes and arranged. Accordingly, when the RGB rotary filter 61 is rotated at a constant speed by the motor 23, the red filter 61*a*, the green filter 61*b*, and the blue filters 61*c* and 61*d* are sequentially interposed on the light path. As a result, a subject anterior to the distal end of the insertion portion 50*a* is sequentially and repetitively illuminated via the light guide 14 by a total of four illumination lights of three types in the order of red, green, blue (for normal light observation) and blue (for fluorescence observation), indicating that blue illumination light is irradiated twice in a row. Incidentally, the wavelength ranges of light transmitted by the respective filters 61*a* to 61*d* are the same as in the first embodiment.

In addition, the blue LED 51 positioned at the distal end portion of the insertion portion 50*a* of the electronic endoscope 50 emits light when the fluorescence observation blue filter 61*d* of the RGB rotary filter 61 is interposed on the light path, and increases illumination light quantity in order to secure an illumination light quantity required during fluorescence observation. The emission timing of the blue LED 51 is controlled by the timing circuit section 64 of the video processor 60.

A timing signal from the timing circuit section 64 is supplied to the normal light CCD control section 25, the fluorescence CCD control section 26, the normal light image video circuit section 62, the fluorescence image video circuit section 63, and the light source section 21 that controls the motor 23 which rotates the RGB rotary filter 61. Consequently, the normal light CCD control section 25 and the fluorescence CCD control section 26 are driven simultaneously. Then, respective image pickup signals of a subject picture under normal light and a fluorescence picture picked up at the same timing are outputted to the normal light image video circuit section 62 and the fluorescence image video circuit section 63. Respective processing by the normal light image video circuit section 62 and the fluorescence image video circuit section 63, as well as the rotation of the RGB rotary filter 61 by the motor 23 are controlled in synchronization by a timing signal from the timing circuit section 64.

As a result, in the same manner as in the first embodiment, image pickup under the RGB frame sequential method is performed by the normal light CCD 11, and a normal color video signal of the subject is obtained at the normal light image video circuit section 62. However, at the normal light image video circuit section 62, a normal light image is created by synchronizing video signals picked up at the timings of the red filter 61*a*, the green filter 61*b* and the normal light observation blue filter 61*c* of the RGB rotary filter 61, and video signals picked up at the timings of the fluorescence observation blue filter 61*d* and the blue LED 51 are not used.

On the other hand, an image pickup signal under fluorescence illuminated by the fluorescence observation blue filter 61*d* and the blue LED 51 of the RGB rotary filter 61 and excited from the subject, and which is capable of being transmitted through the fluorescence transmitting filter 13, as well as an image pickup signal of the subject illuminated via the RGB rotary filter 61, are transferred from the fluorescence CCD 12 to the fluorescence image video circuit section 63.

At the fluorescence image video circuit section 63, an image pickup signal at a timing at which illumination is performed by the normal light observation blue filter 61*c* of the RGB rotary filter 61 is not used, and a fluorescence image is created by synchronizing image pickup signals at a timing at which illumination is performed by the red filter 61*a* and the green filter 61*b* of the RGB rotary filter 61 as well as an image pickup signal under fluorescence. At the image synthesizing circuit section 30, in the same manner as in the first embodiment, image signals outputted from the normal light image video circuit section 62 and the fluorescence image video circuit section 63 are synthesized, and a synthesized image constituted by either one of or both the fluorescence observation image and the normal light observation image is created and outputted to the monitor 2.

In the same manner as in the first embodiment, the endoscope apparatus 40 according to the second embodiment is also capable of simultaneously obtaining a normal light observation image and a fluorescence observation image, thereby eliminating the need of the task of switching between normal light observation and fluorescence observation heretofore required, and improving operability of the observer. In addition, since it is now possible to view images under different observation modes obtained at the same timing, an advantage can be achieved in that comparisons between a fluorescence observation image and a normal light observation image can be performed with greater ease.

Furthermore, with the endoscope apparatus 40 according to the second embodiment, by emitting light from the blue LED 51 at the timing of the fluorescence observation blue filter 61*d* and increasing illumination light quantity, it is now possible to ensure appropriate brightness of both normal light observation images and fluorescence observation images under control that is simpler in comparison with that of the first embodiment.

[Third Embodiment]

Next, a third embodiment of the present invention will be described. Compared to the second embodiment, the objective optical system of the fluorescence CCD 12 of the electronic endoscope 50 has been changed for the third embodiment, and in accordance with the change in the objective optical system, a portion of the functions of the video processor 60 has been changed. Hereinafter, members and circuit sections that perform like operations as the first and second embodiments are assigned like reference characters, and descriptions thereof will be omitted.

Figure 6:
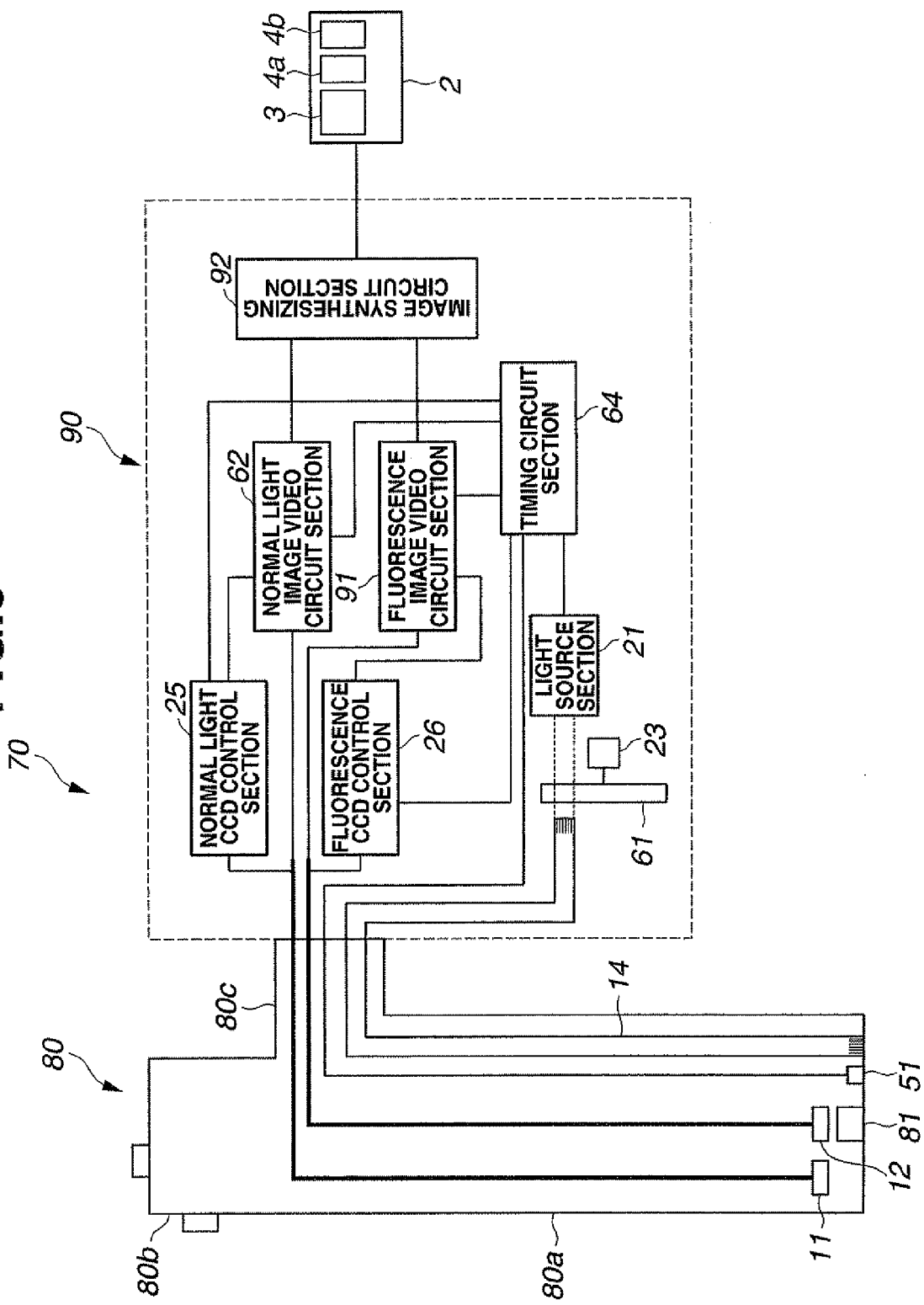
FIG. 6 is a block diagram showing a configuration of an endoscope apparatus according to a third embodiment of the present invention.

As shown in FIG. 6, an endoscope apparatus 70 according to the third embodiment comprises: an electronic endoscope 80 capable of normal light observation and fluorescence observation; and a video processor 90 that drives the electronic endoscope 80, performs signal processing on a normal light observation picture and a fluorescence observation picture from the electronic endoscope 80, and displays a synthesized image on the monitor 2. In a similar manner to the electronic endoscopes 10 and 50 of the first and second embodiments, the electronic endoscope 80 comprises a flexible insertion portion 80*a* and an operation section 80*b* provided at a proximal end side of the insertion portion 80*a*, and is connected to the video processor 90 via a universal cord 80*c* extended from a lateral portion of the operation section 80*b*.

A normal light CCD 11 and a fluorescence CCD 12 are anteriorly oriented and positioned side by side at a distal end portion of the insertion portion 80*a* of the electronic endoscope 80. A blue LED 51 that emits a blue excitation light as an illumination light and which outputs the blue excitation light is positioned alongside an output end of a light guide 14 that irradiates illumination light towards an observation range of an objective optical system of both CCDs 11 and 12.

Figure 7:
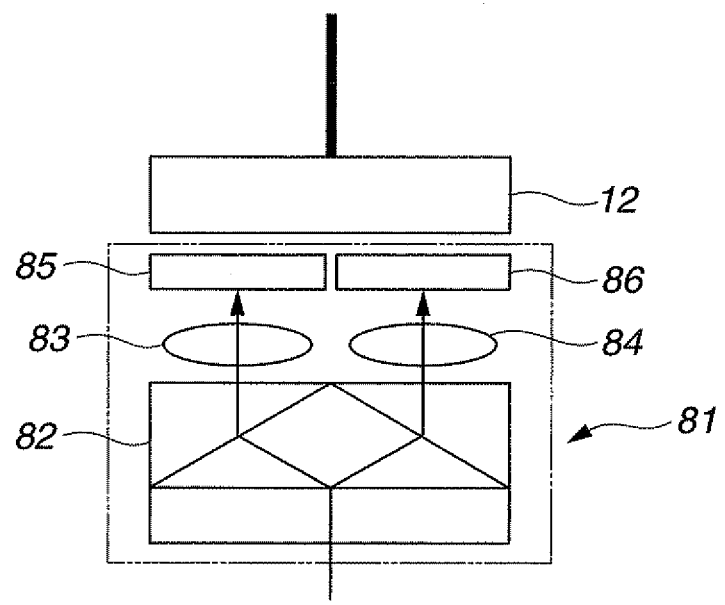
FIG. 7 is an explanatory diagram showing a configuration of an objective optical system on a front face of a fluorescence CCD according to the third embodiment of the present invention.

As shown in FIG. 7, an objective optical system 81 on a front face of the fluorescence CCD 12 is configured so as to bisect reflected light from a subject by a splitter 82 and to form two pictures on an image pickup plane of the fluorescence CCD 12 through lenses 83 and 84. Two filters, namely, a first fluorescence transmitting filter 85 and a second fluorescence transmitting filter 86 are positioned on the front face of the fluorescence CCD 12. Among the filter characteristics shown in FIG. 3 and described in the first embodiment, the first fluorescence transmitting filter 85 has a characteristic of transmitting only wavelengths between 520 nm and 580 nm, while the second fluorescence transmitting filter 86 has a characteristic of transmitting only wavelengths between 580 nm and 700 nm.

The first fluorescence transmitting filter 85 and the second fluorescence transmitting filter 86 are positioned on the front face of the fluorescence CCD 12 so as to respectively cover half of the area of the fluorescence CCD 12. More specifically, the first fluorescence transmitting filter 85 covers one half of the region of the image pickup plane of the fluorescence CCD 12 on a side where images are formed by the lens 83, and the second fluorescence transmitting filter 86 covers the other half of the region of the image pickup plane of the fluorescence CCD 12 on a side where images are formed by the lens 84.

With the video processor 90, in comparison to the second embodiment, the configuration of a light source system (a light source section 21, an RGB rotary filter 61 and a motor 23) is the same, while there is a slight difference in functions related to the creation and synthesis of fluorescence images by the signal processing circuit system. In other words, a subject picture picked up by the normal light CCD 11 is made into an image by the normal light image video circuit section 62 in the same manner as in the second embodiment and a normal light image is created. However, a subject picture picked up by the fluorescence CCD 12 is made into an image by a fluorescence image video circuit section 91.

One half of an image created by the fluorescence image video circuit section 91 is a fluorescence image having a wavelength of 520 nm to 580 nm which is transmitted and obtained through the first fluorescence transmitting filter 85, and the other half is a fluorescence image having a wavelength of 580 nm to 700 nm which is transmitted and obtained through the second fluorescence transmitting filter 86. For example, the fluorescence image at 520 nm to 580 nm is assigned to a G image and the fluorescence image at 580 nm to 700 nm is assigned to an R image, whereby the fluorescence images are outputted to an image synthesizing circuit section 92.

The image synthesizing circuit section 92 synthesizes the normal light image created at the normal light image video circuit section 62 and the fluorescence image created at the fluorescence image video circuit section 91, and outputs the same to the monitor 2 to be displayed. As shown in FIG. 6, the synthesized image outputted to the monitor 2 may either be, for example, a display image in which three images, namely, the normal light observation image 3, a fluorescence observation image 4a transmitted and obtained through the first fluorescence transmitting filter 85 and a fluorescence observation image 4b transmitted and obtained through the second fluorescence transmitting filter 86 are arranged side-by-side, or a display image similar to those in the first and second embodiments.

As seen, in the same manner as in the first and second embodiments, the endoscope apparatus 70 according to the third embodiment is also capable of simultaneously obtaining a normal light observation image and a fluorescence observation image as well as eliminating the need of the task of switching between normal light observation and fluorescence observation heretofore required, thereby improving operability of the observer. In addition, since it is now possible to view images under different observation modes obtained at the same timing, an advantage can be achieved in that comparisons between a fluorescence observation image and a normal light observation image can be performed with greater ease. Furthermore, with the third embodiment, since it is now possible to obtain two types of fluorescence having different wavelengths as shown in FIG. 3 as separate images, improvement of the diagnostic performance of the observer can be achieved.

Incidentally, while the objective optical system 81 described in the third embodiment is arranged as shown in FIG. 7 so that reflected light from a subject is bisected by the splitter 82 and two pictures are formed on the fluorescence CCD 12 by lenses 83 and 84, the first fluorescence transmitting filter 85 and the second fluorescence transmitting filter 86 may be arranged in a mosaic-like pattern and positioned on the front face of the fluorescence CCD 12, whereby a fluorescence observation image transmitted and obtained through the first fluorescence transmitting filter 85 and a fluorescence observation image transmitted and obtained through the second fluorescence transmitting filter 86 are separated and made into images under readout control at the fluorescence image video circuit section 91.

[Fourth Embodiment]

Figure 8:
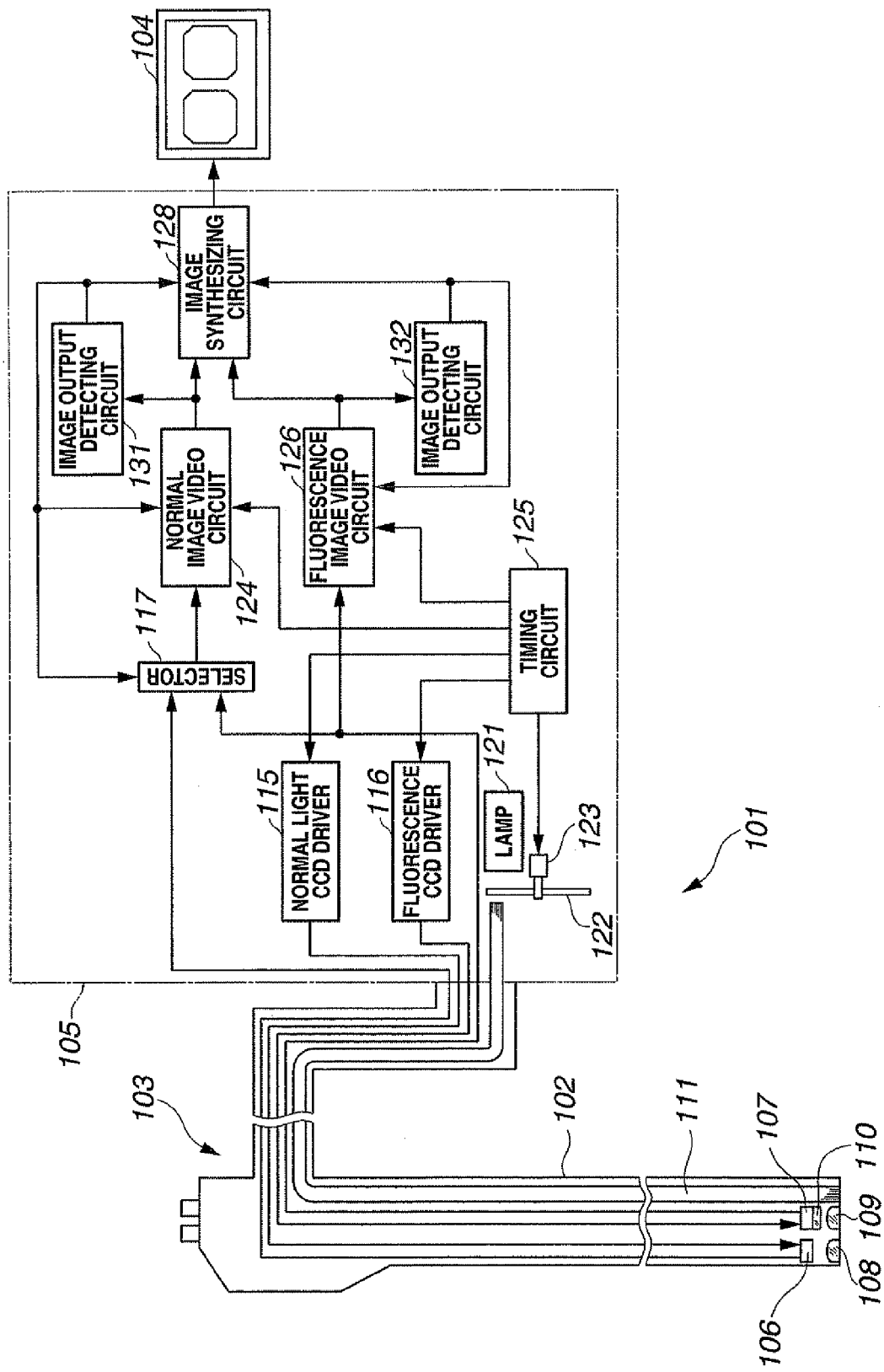
FIG. 8 is a configuration diagram showing a configuration of an endoscope apparatus according to a fourth embodiment of the present invention.

Next, a fourth embodiment of the present invention will be described. As shown in FIG. 8, an endoscope apparatus 101 according to the fourth embodiment comprises: an electronic endoscope 103 having a flexible insertion portion 102 and which is capable of normal light observation and fluorescence observation; and a video processor 105 that drives the electronic endoscope 103, performs signal processing on a normal light observation picture and a fluorescence observation picture from the electronic endoscope 103, and displays a normal light observation image and a fluorescence observation image on a monitor 104.

Two, namely, first and second solid state image pickup devices or, more specifically, a normal light CCD 106 that is normal light image pickup means and a fluorescence CCD 107 that is fluorescence image pickup means are anteriorly oriented and positioned side by side at a distal end of the insertion portion 102 of the electronic endoscope 103. For example, a monochrome charge-coupled device (CCD) is used as both the normal light CCD 106 and the fluorescence CCD 107.

Objective optical systems 108 and 109 are respectively positioned anterior to both the normal light CCD 106 and the fluorescence CCD 107, whereby a picture of an anterior subject is formed on both the normal light CCD 106 and the fluorescence CCD 107. Incidentally, both the normal light CCD 106 and the fluorescence CCD 107 may be arranged to share a single objective optical system.

A fluorescence transmitting filter 110 that transmits only light having a wavelength of 520 nm to 600 nm is positioned between the fluorescence CCD 107 and the objective optical system 109. No such a filter is positioned anterior to the normal light CCD 106.

An output end of an illumination light guide fiber bundle 111 that irradiates illumination light towards the observation ranges of both objective optical systems 108 and 109 is positioned alongside both objective optical systems 108 and 109.

A light source lamp 121 for supplying illumination light to the illumination light guide fiber bundle 111 and constituted by, for example, a xenon lamp is positioned in the video processor 105, and an RGB rotary filter 122 is positioned in an illumination light path between the light source lamp 121 and an incident end of the illumination light guide fiber bundle 111.

Figure 9:
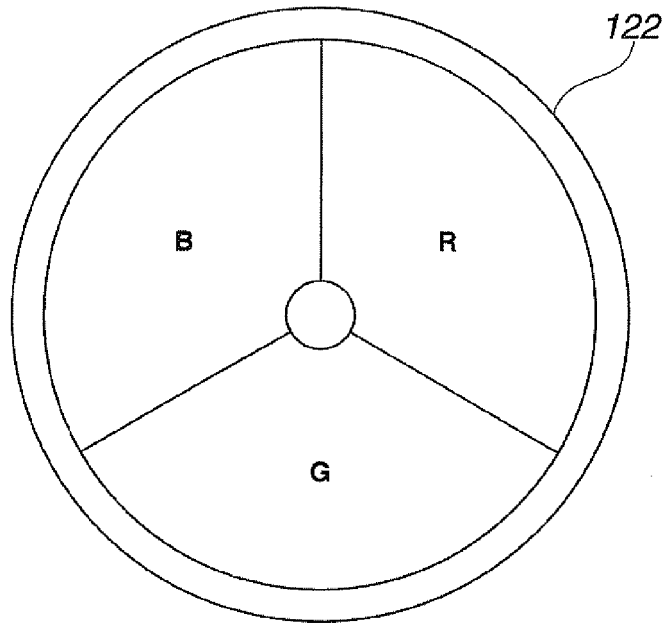
FIG. 9 is a diagram showing a configuration of the RGB rotary filter shown in FIG. 8, according to the fourth embodiment of the present invention.

As shown in FIG. 9, the RGB rotary filter 122 is constituted by three filters respectively colored red (R), green (G) and blue (B) and formed in fan-like shapes, and is rotated at a constant speed by a motor 123.

Incidentally, the wavelength ranges of light transmitted by the respective color filters are, for example, as described below. Red (R): 580 nm to 650 nm. Green (G): 500 nm to 580 nm. Blue (B): 400 nm to 500 nm.

Consequently, a subject anterior to a distal end of the insertion portion 102 is sequentially and repetitively illuminated via the illumination light guide fiber bundle 111 by illumination lights having the three colors of red, green and blue.

The normal light CCD 106 is driven by a normal light CCD driver 115 that is normal light image pickup driving means, and an image pickup signal thereof is outputted via a selector 117 to a normal image video circuit 124, which is normal light image signal processing means, in the video processor 105.

On the other hand, the fluorescence CCD 107 anteriorly provided with the fluorescence transmitting filter 110 is driven by a fluorescence CCD driver 116 that is fluorescence image pickup driving means, and an image pickup signal thereof is outputted to a fluorescence image video circuit 126, which is fluorescence image signal processing means, in the video processor 105.

Incidentally, an image pickup signal of the fluorescence CCD 107 can be outputted to the normal image video circuit 124 via the selector 117.

In addition, the driving of the normal light CCD 106 and the fluorescence CCD 107 (the driving by the normal light CCD driver 115 and the fluorescence CCD driver 116), processing by the normal image video circuit 124 and the fluorescence image video circuit 126, and the rotation of the motor 123 that rotates the RGB rotary filter 122 are controlled in synchronization by an output signal from a timing circuit 125.

As a result, image pickup under the so-called RGB frame sequential method is performed at the normal light CCD 106, and a normal color video signal of the subject is obtained at the normal image video circuit 124.

On the other hand, from a video signal picked up by the fluorescence CCD 107 and transferred to the fluorescence image video circuit 126, only a video signal during illumination of the subject by a blue illumination light (wavelength of 400 nm to 500 nm) is extracted at the fluorescence image video circuit 126. In other words, since an image obtained by the fluorescence CCD 107 is limited to pictures under light whose wavelength can be transmitted through the fluorescence transmitting filter 110, a fluorescence image excited from the subject by an excitation light having a wavelength of 400 nm to 500 nm included in the blue illumination light is extracted at the fluorescence image video circuit 126.

A fluorescence image signal outputted from the fluorescence image video circuit 126 and a color image signal outputted from the normal image video circuit 124 is inputted to an image synthesizing circuit 128 that is image synthesizing means provided with notifying means. Image synthesis processing performed by the image synthesizing circuit 128 causes a synthesized image constituted by either one of or both the fluorescence image and the normal image to be displayed on the monitor 104.

The color image signal outputted from the normal image video circuit 124 is also inputted to a first image output detecting circuit 131 that is normal light image processing monitoring means, and the fluorescence image signal outputted from the fluorescence image video circuit 126 is also inputted to a second image output detecting circuit 132 that is fluorescence image processing monitoring means.

The first image output detecting circuit 131 and the second image output detecting circuit 132 have the same configuration, and are arranged to detect output of respective image signals and based on the detection result, exercise switching control of the selector, processing control at the normal image video circuit 124 and the fluorescence image video circuit 126, and image synthesis control at the image synthesizing circuit 128.

Figure 10:
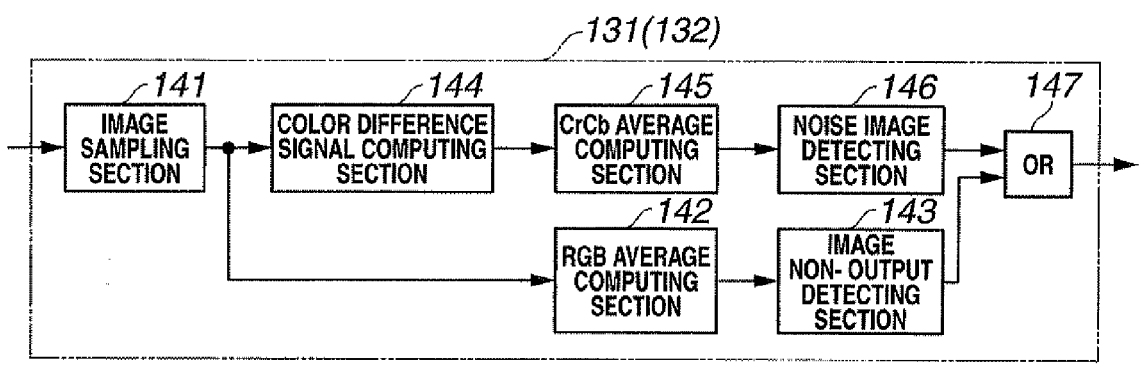
FIG. 10 is a block diagram showing a configuration of the first image output detecting circuit or the second image output detecting circuit shown in FIG. 8, according to the fourth embodiment of the present invention.

More specifically, as shown in FIG. 10, the first image output detecting circuit 131 (or the second image output detecting circuit 132) is configured so as to comprise: an image sampling section 141 that samples color image signals outputted from the normal image video circuit 124; an RGB average computing section 142 that computes averages of R/G/B images sampled by the image sampling section 141; an image non-output detecting section 143 that detects non-output of images based on the computation results of the RGB average computing section 142; a color difference signal computing section 144 that computes color difference signals from R/G/B images sampled by the image sampling section 141; a CrCb average computing section 145 that computes averages of the color difference signals computed by the color difference signal computing section 144; a noise image detecting section 146 that detects a noise image based on the computation results of the CrCb average computing section 145; and an OR circuit section 147 that performs an OR on the detection result of the image non-output detecting section 143 and the detection result of the noise image detecting section 146 and outputs the same as an output abnormality occurrence signal of the image output detecting circuit.

The image sampling section 141 samples R, G and B data values from an endoscopic image portion excluding a character region, and outputs the same to the RGB average computing section 142 and the color difference signal computing section 144.

The RGB average computing section 142 calculates averages of one screen's worth of R, G and B data values, and outputs the same to the image non-output detecting section 143.

When the image non-output detecting section 143 detects that averages of R, G and B data values are all "0" for a plurality of screens, the image non-output detecting section 143 assumes a non-output of an image signal and outputs an image non-output signal to the OR circuit section 147.

In addition, the color difference signal computing section 144 calculates color difference signals Cr, Cb from the R, G and B data values. The CrCb average computing section 145 calculates averages of one screen's worth of Cr, Cb, and outputs the same to the noise image detecting section 146.

$$Cr = 0.5R - 0.419G - 0.081B$$

$$Cb = -0.169R - 0.331G + 0.5B$$

Figure 11:
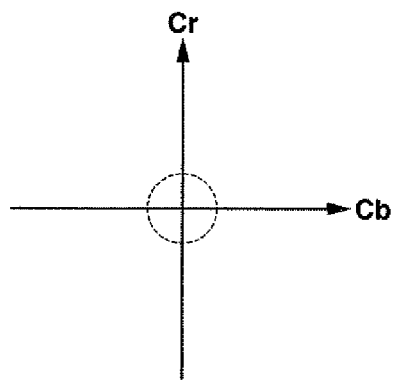
FIG. 11 is a diagram showing a Cr-Cb color plane for explaining operations of the noise image detecting section shown in FIG. 10, according to the fourth embodiment of the present invention.

Based on the averages of Cr, Cb, the noise image detecting section 146 detects whether an image signal is a noise image according to a location thereof on Cr-Cb color plane coordinates shown in FIG. 11, and outputs the detection result to the OR circuit section 147.

Incidentally, in general, various color components randomly occur in a noise image and averages of Cr, Cb are distributed in the vicinity of the origin of the Cr-Cb color plane coordinates. Therefore, for the present embodiment, a noise image is assumed in a case where the averages of Cr, Cb fall within a dotted line on the Cr-Cb color plane coordinates shown in FIG. 11. The noise image occurrence signal is then outputted to the OR circuit section 147.

Based on the image non-output signal from the image non-output detecting section 143 or the noise image occurrence signal from the noise image detecting section 146, when the OR circuit section 147 determines that an image signal is not normally outputted, the OR circuit section 147 outputs an output abnormality occurrence signal to the selector 117, the normal image video circuit 124, the fluorescence image video circuit 126 and the image synthesizing circuit 128.

Based on the output abnormality occurrence signal, in a case where, for example, an abnormality exists in the fluorescence image, only the normal light image is displayed on the monitor 104. In addition, in a case where an abnormality exists in the normal light image, the fluorescence image is outputted via the selector 117 to the normal image video circuit 124 and a quasi-normal light image is created from the fluorescence image and displayed on the monitor 104. Display examples of the monitor 104 are shown in FIGS. 12 to 25. The display may be arranged to be selectable.

A quasi-normal image is an image created as a normal image by inputting an output of the fluorescence CCD 107 to the normal image video circuit 124. Since the fluorescence transmitting filter 110 that cuts off excitation light is provided on a front face of the fluorescence CCD 107, the blue color tone differs slightly in comparison with a normal image. However, the level is sufficient as a temporary image.

Figure 12:
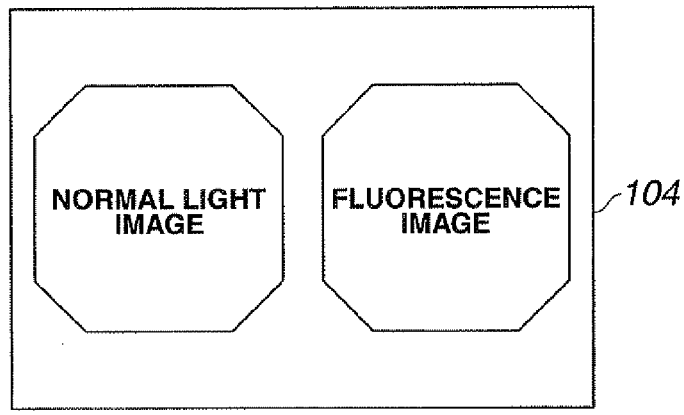
FIG. 12 is a first diagram showing a monitor display example for explaining operations of the video processor shown in FIG. 8, according to the fourth embodiment of the present invention.

(1) FIG. 12 is a display example in a case where both a normal light image and a fluorescence image are normal. The normal light image and the fluorescence image are displayed on the monitor 104.

Figure 13:
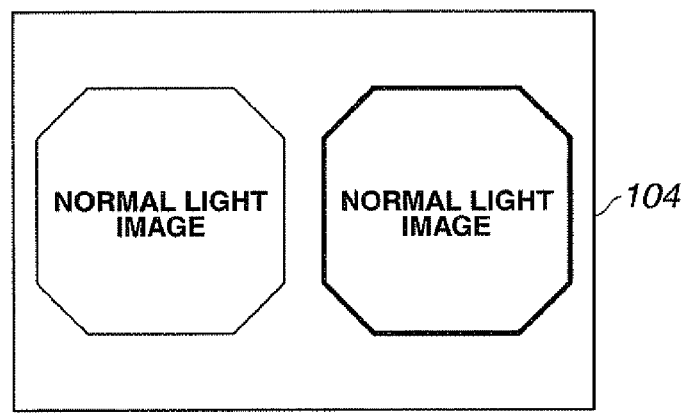
FIG. 13 is a second diagram showing a monitor display example for explaining operations of the video processor shown in FIG. 8, according to the fourth embodiment of the present invention.

(2) FIG. 13 is a display example in a case where a normal light image is normal and a fluorescence image is abnormal. The normal light image is displayed on the monitor 104 as well as in a region in which the fluorescence image is to be displayed. In this case, the image synthesizing circuit 128 includes notifying means, whereby a notification that the fluorescence image is abnormal is performed by having the notifying means of the image synthesizing circuit 128 change, for example, the frame of the normal light image in the region in which the fluorescence image is displayed is indicated with heavy lines.

Through the notification, since an operator can readily perform visual confirmation of the occurrence of a problem in fluorescence observation, appropriate responses can be taken. In addition, since a patient is unable to determine whether a procedural problem has occurred just by the image on the monitor 104, the patient need not experience anxiety.

Figure 14:
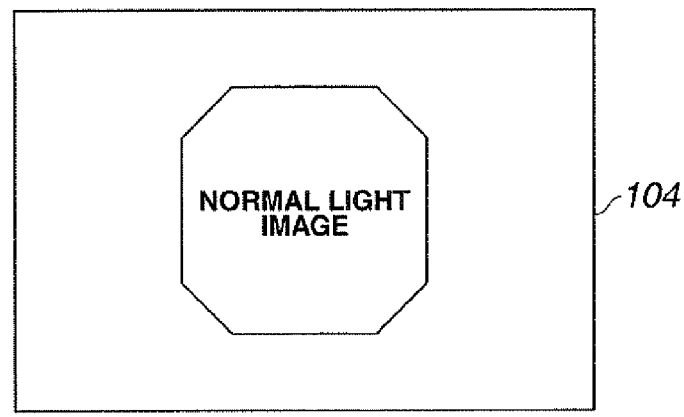
FIG. 14 is a third diagram showing a monitor display example for explaining operations of the video processor shown in FIG. 8, according to the fourth embodiment of the present invention.

(3) FIG. 14 is a display example in a case where a normal light image is normal and a fluorescence image is abnormal. The normal light image is displayed in a central region of the monitor 104. The notifying means of the image synthesizing circuit 128 performs notification of an abnormality in the fluorescence image through this display mode.

Figure 15:
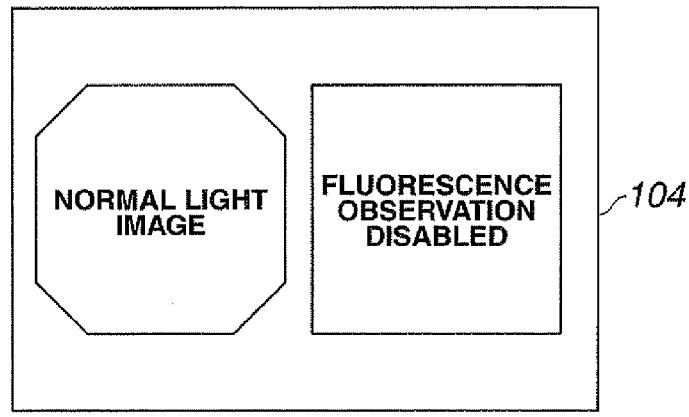
FIG. 15 is a fourth diagram showing a monitor display example for explaining operations of the video processor shown in FIG. 8, according to the fourth embodiment of the present invention.

(4) FIG. 15 is a display example in a case where a normal light image is normal and a fluorescence image is abnormal. The notifying means of the image synthesizing circuit 128 displays the normal light image on the monitor 104, and displays a message to the effect that fluorescence observation is disabled in the region in which the fluorescence image is to be displayed.

As for the message, besides "fluorescence observation disabled", messages such as "fluorescence observation aborted", "only normal light observation available", "fluorescence observation unavailable" or "only normal light observation" may be used.

Figure 16:
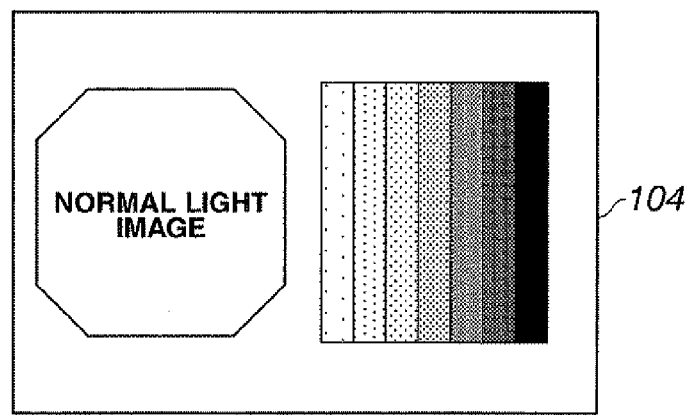
FIG. 16 is a fifth diagram showing a monitor display example for explaining operations of the video processor shown in FIG. 8, according to the fourth embodiment of the present invention.

(5) FIG. 16 is a display example in a case where a normal light image is normal and a fluorescence image is abnormal. The notifying means of the image synthesizing circuit 128 displays the normal light image on the monitor 104, and displays a color bar in the region in which the fluorescence image is to be displayed.

Figure 17:
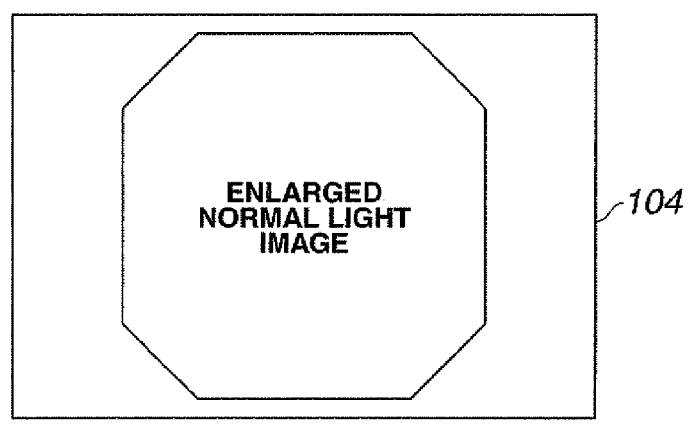
FIG. 17 is a sixth diagram showing a monitor display example for explaining operations of the video processor shown in FIG. 8, according to the fourth embodiment of the present invention.

(6) FIG. 17 is a display example in a case where a normal light image is normal and a fluorescence image is abnormal. The notifying means of the image synthesizing circuit 128 displays an enlarged image of the normal light image in a central region of the monitor 104.

Figure 18:
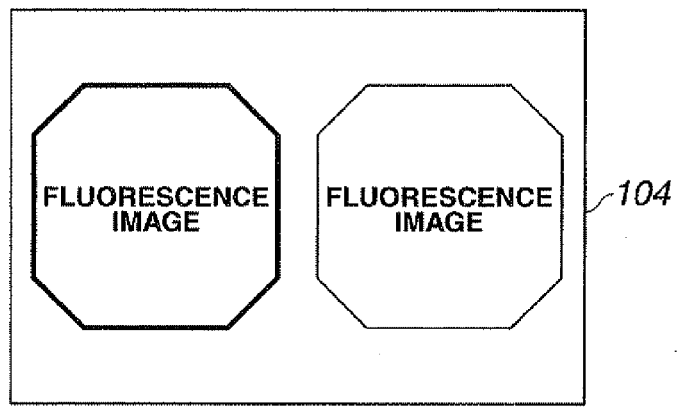
FIG. 18 is a seventh diagram showing a monitor display example for explaining operations of the video processor shown in FIG. 8, according to the fourth embodiment of the present invention.

(7) FIG. 18 is a display example in a case where a normal light image is abnormal and a fluorescence image is normal. The notifying means of the image synthesizing circuit 128 displays the fluorescence image on the monitor 104 as well as in the region in which the normal light image is to be displayed. In this case, the notifying means image synthesizing circuit 128 notifies that the normal light image is abnormal by, for example, changing the frame of the fluorescence image in the region in which the normal light image is to be displayed to heavy lines.

Figure 19:
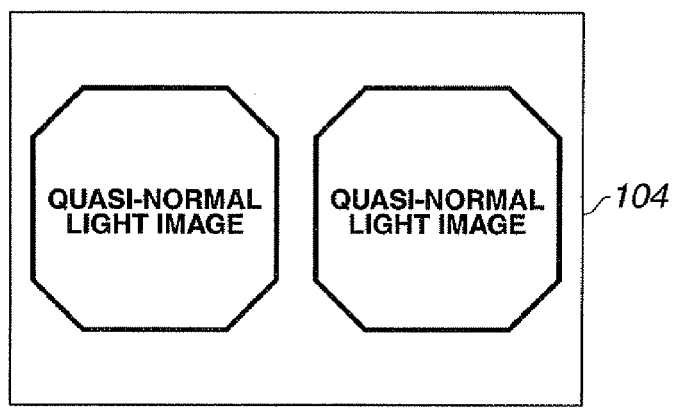
FIG. 19 is an eighth diagram showing a monitor display example for explaining operations of the video processor shown in FIG. 8, according to the fourth embodiment of the present invention.

(8) FIG. 19 is a display example in a case where a normal light image is abnormal and a fluorescence image is normal. The notifying means of the image synthesizing circuit 128 displays a quasi-normal light image created based on the fluorescence image respectively in place of the normal light image and the fluorescence image, and at the same time, notifies that the normal light image is abnormal by changing the frame of the quasi-normal light images to heavy lines.

Figure 20:
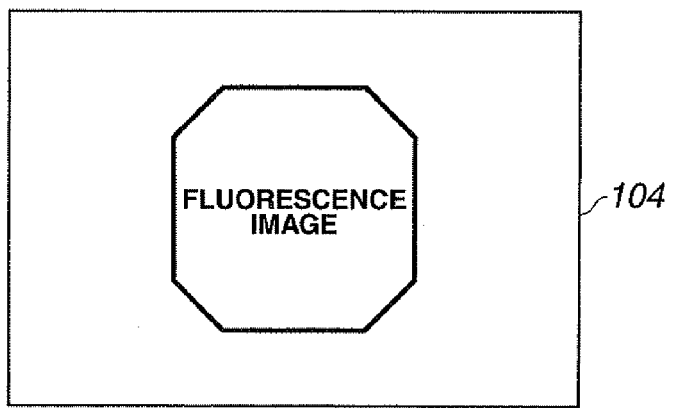
FIG. 20 is a ninth diagram showing a monitor display example for explaining operations of the video processor shown in FIG. 8, according to the fourth embodiment of the present invention.

(9) FIG. 20 is a display example in a case where a normal light image is abnormal and a fluorescence image is normal. The notifying means of the image synthesizing circuit 128 displays an enlarged image of the fluorescence image in a central region of the monitor 104, and at the same time, notifies that the normal light image is abnormal by changing the frame of the enlarged fluorescence image to heavy lines.

Figure 21:
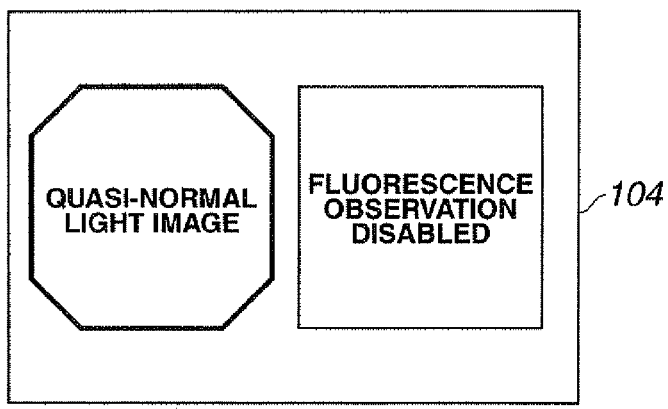
FIG. 21 is a tenth diagram showing a monitor display example for explaining operations of the video processor shown in FIG. 8, according to the fourth embodiment of the present invention.

(10) FIG. 21 is a display example in a case where a normal light image is abnormal and a fluorescence image is normal. The notifying means of the image synthesizing circuit 128 displays a quasi-normal light image on the monitor 104, and at the same time, displays a message to the effect that fluorescence observation is disabled in the region in which the fluorescence image is to be displayed. Notification that the normal light image is abnormal is made by changing the frame of the quasi-normal light image to heavy lines.

Figure 22:
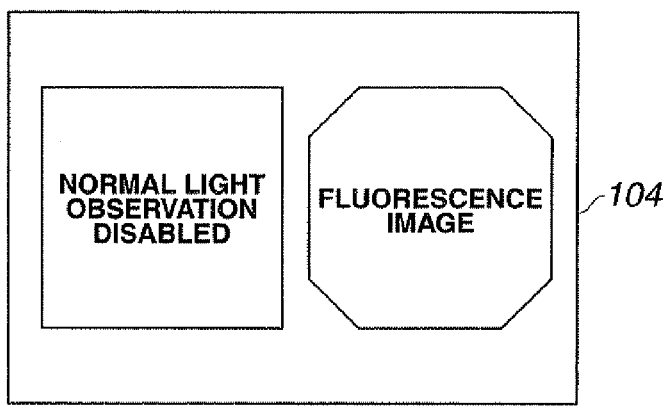
FIG. 22 is an eleventh diagram showing a monitor display example for explaining operations of the video processor shown in FIG. 8, according to the fourth embodiment of the present invention.

(11) FIG. 22 is a display example in a case where a normal light image is abnormal and a fluorescence image is normal. The notifying means of the image synthesizing circuit 128 displays the fluorescence image on the monitor 104, and at the same time, displays a message to the effect that normal light observation is disabled in the region in which the normal light image is to be displayed.

Figure 23:
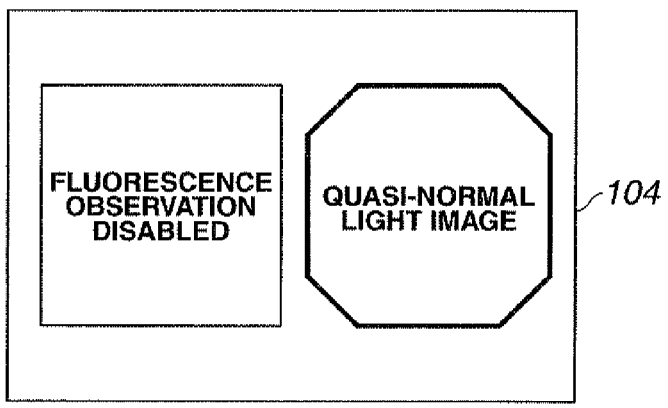
FIG. 23 is a twelfth diagram showing a monitor display example for explaining operations of the video processor shown in FIG. 8, according to the fourth embodiment of the present invention.

(12) FIG. 23 is a display example in a case where a normal light image is abnormal and a fluorescence image is normal. The notifying means of the image synthesizing circuit 128 displays a quasi-normal light image on the monitor 104, and at the same time, displays a message to the effect that fluorescence observation is disabled in the region in which the normal light image is to be displayed. Notification that the normal light image is abnormal is made by changing the frame of the quasi-normal light image to heavy lines.

Figure 24:
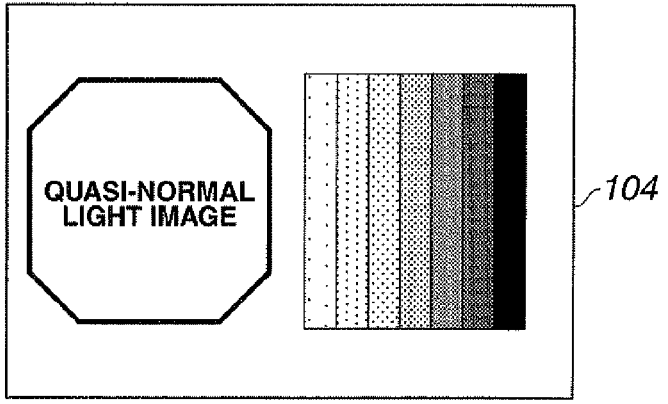
FIG. 24 is a thirteenth diagram showing a monitor display example for explaining operations of the video processor shown in FIG. 8, according to the fourth embodiment of the present invention.

(13) FIG. 24 is a display example in a case where a normal light image is abnormal and a fluorescence image is normal. The notifying means of the image synthesizing circuit 128 displays a quasi-normal light image on the monitor 104, and at the same time, displays a color bar in the region in which the fluorescence image is to be displayed. Notification that the normal light image is abnormal is made by changing the frame of the quasi-normal light image to heavy lines.

Figure 25:
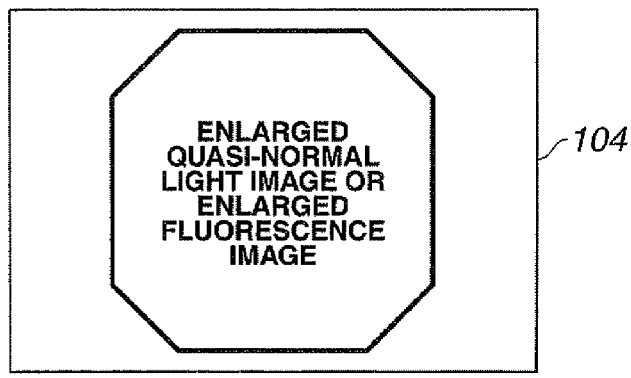
FIG. 25 is a fourteenth diagram showing a monitor display example for explaining operations of the video processor shown in FIG. 8, according to the fourth embodiment of the present invention.

(14) FIG. 25 is a display example in a case where a normal light image is abnormal and a fluorescence image is normal. The notifying means of the image synthesizing circuit 128 displays an enlarged image of a quasi-normal light image or the fluorescence image in a central region of the monitor 104. Notification that the normal light image is abnormal is made by changing the frame of the enlarged quasi-normal light image or fluorescence image to heavy lines.

As seen, with the present embodiment, in a case where a failure or the like occurs in one of the CCDs, the operator is notified of the occurrence of the failure or the like by the display mode of the monitor display. Therefore, visual confirmation of the occurrence of the failure or the like can be readily performed to enable appropriate responses to be taken, and no anxiety will be given to patients and the like.

In addition, in a case where a failure and the like occurs at the normal light CCD 106, since continuation of normal light observation is made possible through a quasi-normal light image using the fluorescence CCD 107, therapeutic response becomes possible in an environment closely resembling images that the operator is familiar with.

Figure 26:
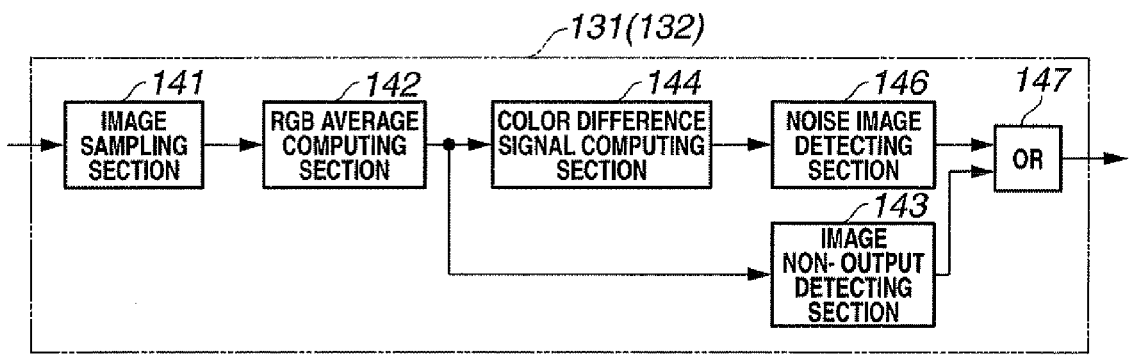
FIG. 26 is a block diagram showing a configuration of a modification of the first image output detecting circuit or the second image output detecting circuit shown in FIG. 10, according to the fourth embodiment of the present invention.

Incidentally, as shown in FIG. 26, the first image output detecting circuit 131 (or the second image output detecting circuit 132) may be alternatively configured so as to comprise: the image sampling section 141 that samples color image signals outputted from the normal image video circuit 124; the RGB average computing section 142 that computes averages of R/G/B images sampled by the image sampling section 141; the image non-output detecting section 143 that detects non-output of images based on the computation results of the RGB average computing section 142; the color difference signal computing section 144 that computes color difference signals from averages of RIG/B images from the RGB average computing section 142; the noise image detecting section 146 that detects a noise image based on the computation results of the color difference signal computing section 144; and the OR circuit section 147 that performs an OR on the detection result of the image non-output detecting section 143 and the detection result of the noise image detecting section 146 and outputs the same as an output abnormality occurrence signal of the image output detecting circuit.

In this configuration, instead of Cr, Cb, the color difference signal computing section 144 computes single screen averages R−Y, B−Y of R, G, and B data values after sampling.

$$R-Y=0.7R-0.59G-0.11B$$

$$B-Y=-0.3R-0.59G-0.89B$$

Figure 27:
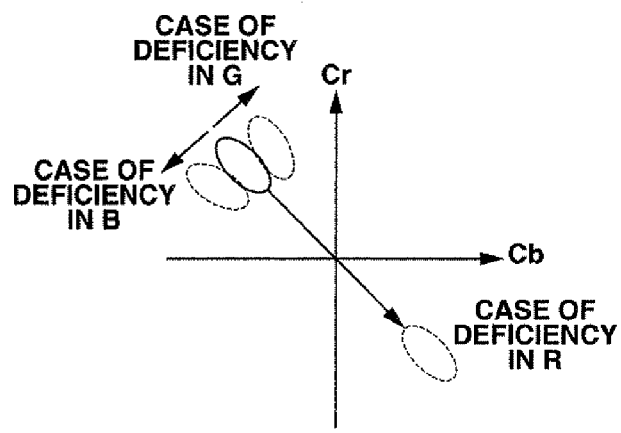
FIG. 27 is a diagram showing a Cr-Cb color plane for explaining a modification of operations of the noise image detecting section shown in FIG. 10, according to the fourth embodiment of the present invention.

In addition, while a noise image is assumed when falling within the dotted line on the Cr-Cb color plane coordinates shown in FIG. 11, the noise image detecting section 146 may be arranged to detect a noise image occurrence when any of the outputs of the R, G, and B data values becomes "0" and upon detection of a biased distribution on the Cr-Cb color plane coordinates as shown in FIG. 27.

Furthermore, in order to improve the accuracy of noise image detection and image non-output detection, an image may be arranged to be segmented into blocks, whereby an average is calculated for each block, and noise image detection and image non-output detection is performed accordingly. Moreover, noise image detection may be performed using known frequency analysis.

Figure 28:
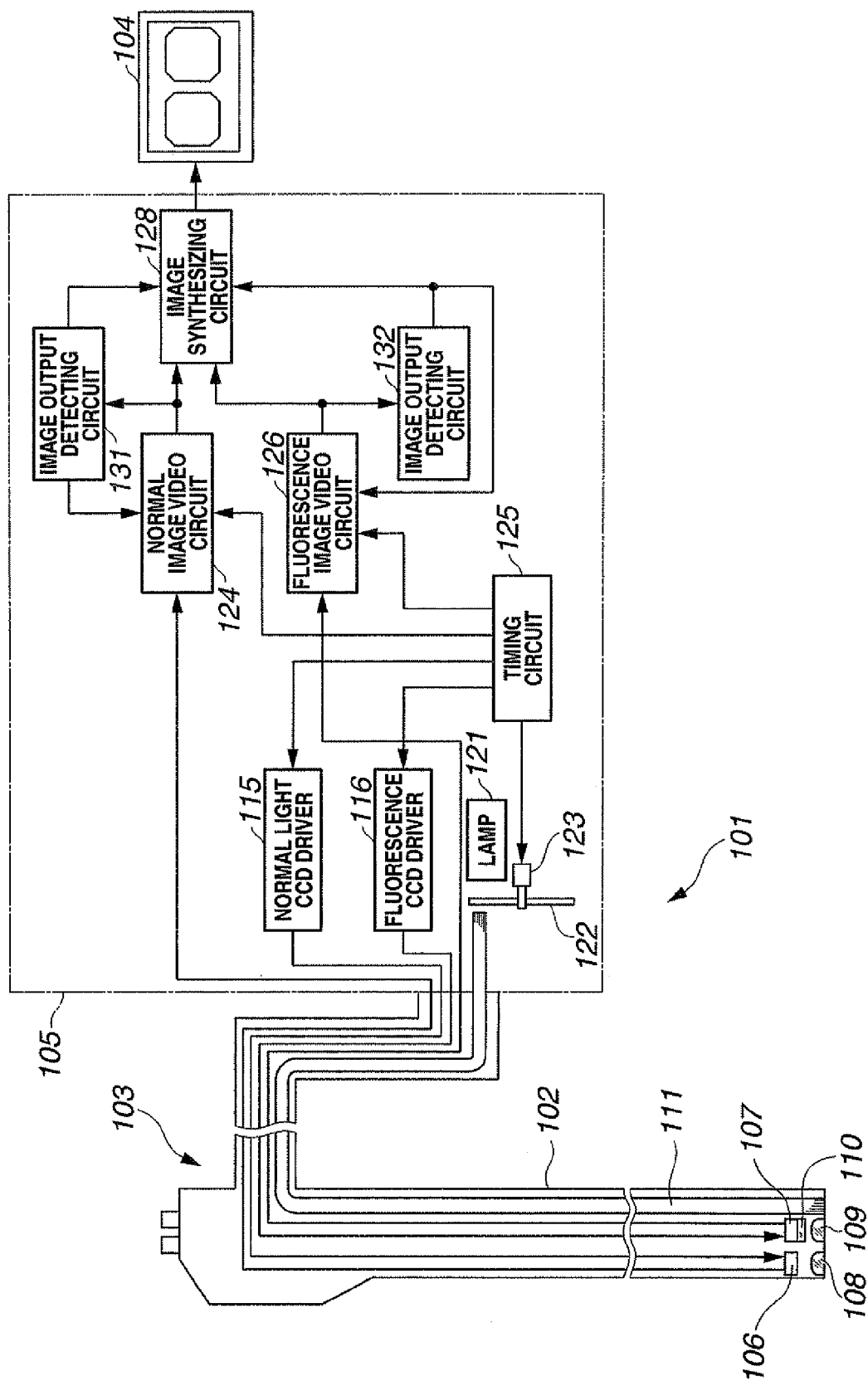
FIG. 28 is a diagram showing a configuration of a first modification of the video processor shown in FIG. 8, according to the fourth embodiment of the present invention.

Incidentally, while the selector 117 is used in the present embodiment, the selector can be omitted by the configuration shown in FIG. 28.

Figure 29:
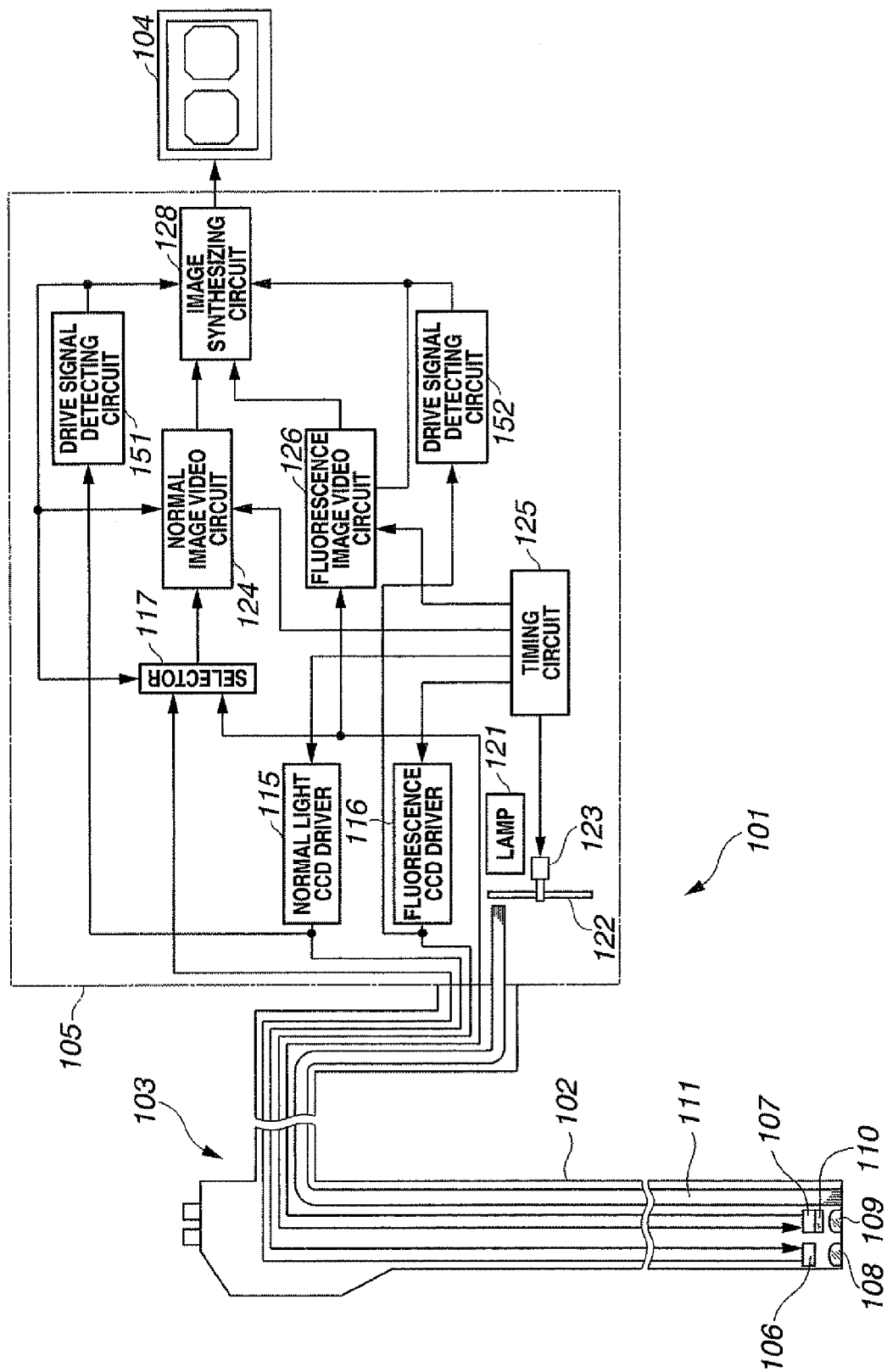
FIG. 29 is a diagram showing a configuration of a second modification of the video processor shown in FIG. 8, according to the fourth embodiment of the present invention.

In addition, while the video processor 105 according to the present embodiment is arranged to perform signal processing on a color image signal outputted from the normal image video circuit 124 and a fluorescence image signal outputted from the fluorescence image video circuit 126 at the first image output detecting circuit 131 and the second image output detecting circuit 132 to detect an abnormality of the normal light CCD 106 or the fluorescence CCD 107, the present invention is not limited to this arrangement. Instead, as a first modification of the video processor 105, as shown in FIG. 29, drive signal detecting circuits 151 and 152 which respectively detect drive signals of the normal light CCD driver 115 that drives the normal light CCD 106 and the fluorescence CCD driver 116 that drives the fluorescence CCD 107 may be provided in place of the image output detecting circuits, whereby failures and the like of the CCDs are detected by monitoring the driving states of the normal light CCD driver 115 and the fluorescence CCD driver 116, and a selector and the like is controlled in the same manner as is the case with the image output detecting circuits.

Figure 30:
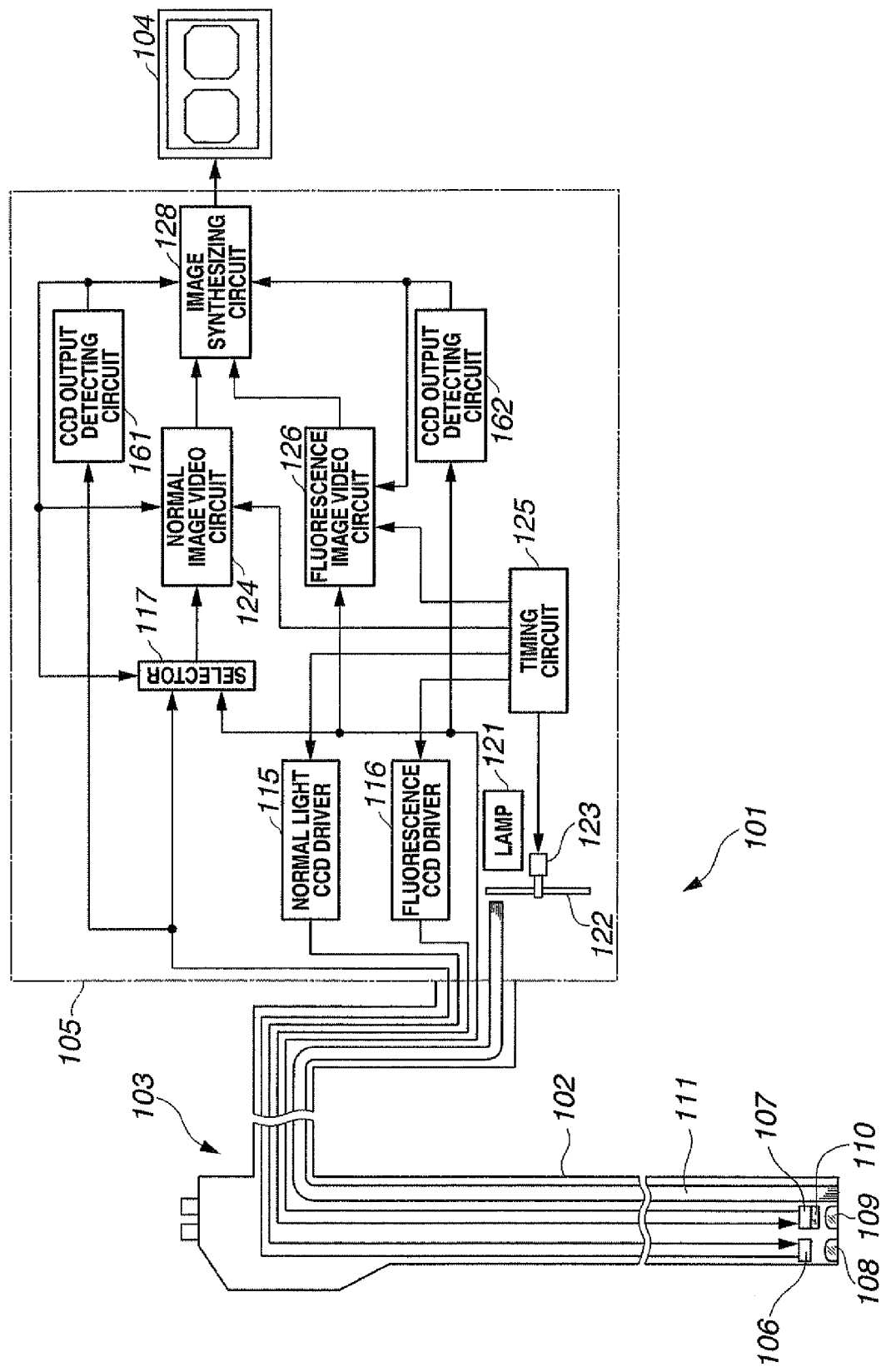
FIG. 30 is a diagram showing a configuration of a third modification of the video processor shown in FIG. 8, according to the fourth embodiment of the present invention.

Furthermore, as a second modification of the video processor 105, as shown in FIG. 30, CCD output detecting circuits 161 and 162 that respectively detect image pickup signals from the normal light CCD 106 and the fluorescence CCD 107 may be provided in place of the image output detecting circuits, whereby failures and the like of the CCDs are detected by directly monitoring the output states of the normal light CCD driver 115 and the fluorescence CCD driver 116, and a selector and the like is controlled in the same manner as was the case with the image output detecting circuits.

Figure 31:
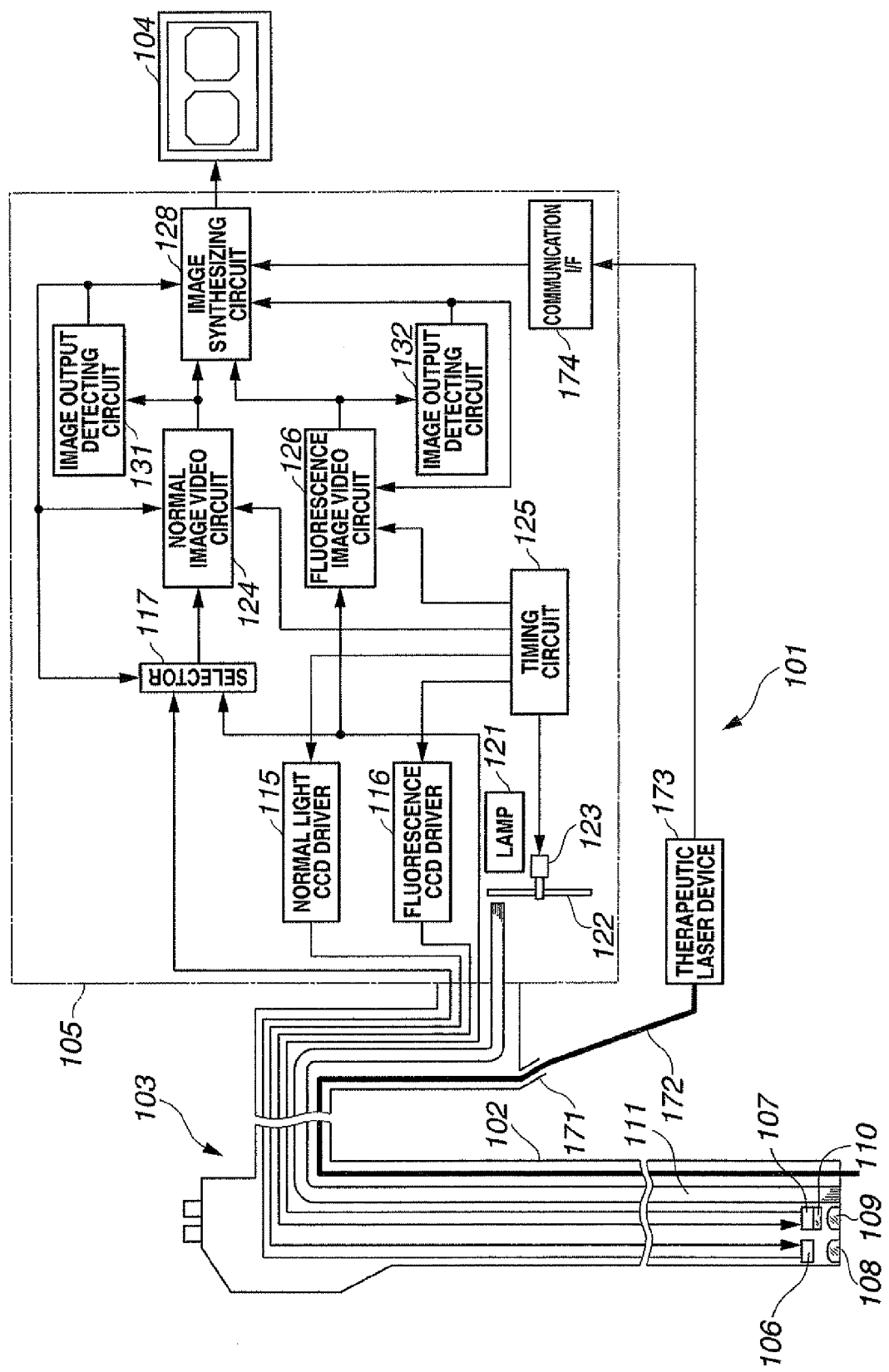
FIG. 31 is a diagram showing a configuration of a fourth modification of the video processor shown in FIG. 8, according to the fourth embodiment of the present invention.

Incidentally, as shown in FIG. 31, the endoscope apparatus 101 according to the present embodiment uses, for example, a therapeutic laser device 173 that inserts a probe 172 through a treatment instrument channel 171 and the like of the electronic endoscope 103 in order to treat a diseased part.

When treatment by such a therapeutic laser device 173 is performed, laser light is irradiated from a distal end of the probe 172 to the diseased part. Since fluorescence from a living body is generally weak, the gain of an image pickup signal from the fluorescence CCD 107 is set higher than the gain of an image pickup signal from the normal light CCD 106. When the laser light irradiates the diseased part, halation may occur in an image from the fluorescence CCD 107 or noise may be amplified in the image.

In this light, the video processor 105 shown in FIG. 31 is provided with a communication interface (hereinafter "communication I/F") 174 for inputting an operation signal of the therapeutic laser device 173, whereby, when it is detected that the therapeutic laser device 173 has been operated via the communication I/F 174, the image synthesizing circuit 128 is controlled and the fluorescence image is erased from the monitor display as shown in FIG. 14. At this point, while it is also possible to display the image by enlarging the image size to full screen, there are cases where an operator does not welcome changes in image size. Therefore, by enabling an image size to be designated at this point through a menu or the like, the apparatus becomes suitable to the preferences of the user. Moreover, the switching itself among screens during use of the therapeutic laser device 173 may be arranged to be selectable by the user through a menu or the like. In addition to the therapeutic laser device 173, similar operations are performed when using an electric scalpel.

In the configuration shown in FIG. 31, since switching to a normal light image is automatically performed when using the therapeutic laser device 173 or an electric scalpel, display of a noise-amplified image can be prevented without troubling the operator.

Figure 32:
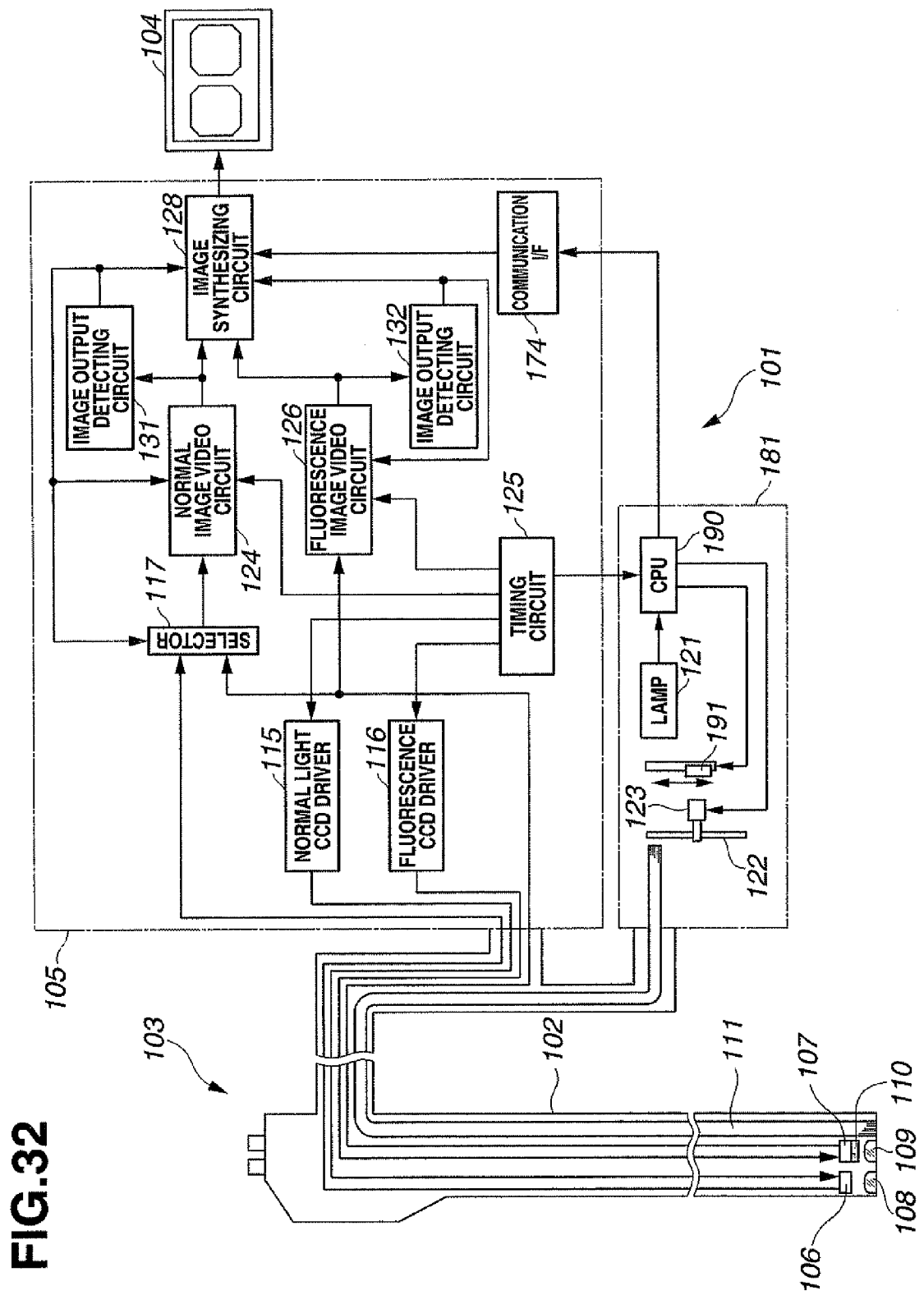
FIG. 32 is a diagram showing a configuration of a fifth modification of the video processor shown in FIG. 8, according to the fourth embodiment of the present invention.

In addition, while the video processor 105 according to the present embodiment has built-in light source means, a light source device 181 may be provided separate from the video processor 105 as shown in FIG. 32. A light source device 181 of this kind monitors the lighting state of the light source lamp 121 by a CPU 190 or the like, and when it is detected that the light source lamp 121 cannot be lighted due to failure or the like, illumination light is supplied by interposing an emergency light on the light path. Monitoring of the lighting of the light source lamp 121 is performed by monitoring the value of a current flowing through the light source lamp 121.

With the configuration shown in FIG. 32, when the CPU 190 performs switching control to the emergency light 191, a switching signal from the CPU 190 is transferred to the image synthesizing circuit 128 via the communication I/F 174 of the video processor 105. Based on the switching signal, the image synthesizing circuit 128 releases simultaneous display of the normal light image and the fluorescence image, and displays only the normal light image on the monitor as shown in FIG. 14. Again, the image size at this point may be arranged as to be designated through a menu or the like.

Furthermore, based on the switching signal, the image synthesizing circuit 128 may display the normal light image in the fluorescence image display region as shown in FIG. 13 so that two screens of the same normal light image are displayed side-by-side. In this case, since both the image size and the image position remain unchanged, there is no need to move the operators viewpoint. As a result, fatigue of the operator can be reduced.

[Fifth Embodiment]

Figure 33:
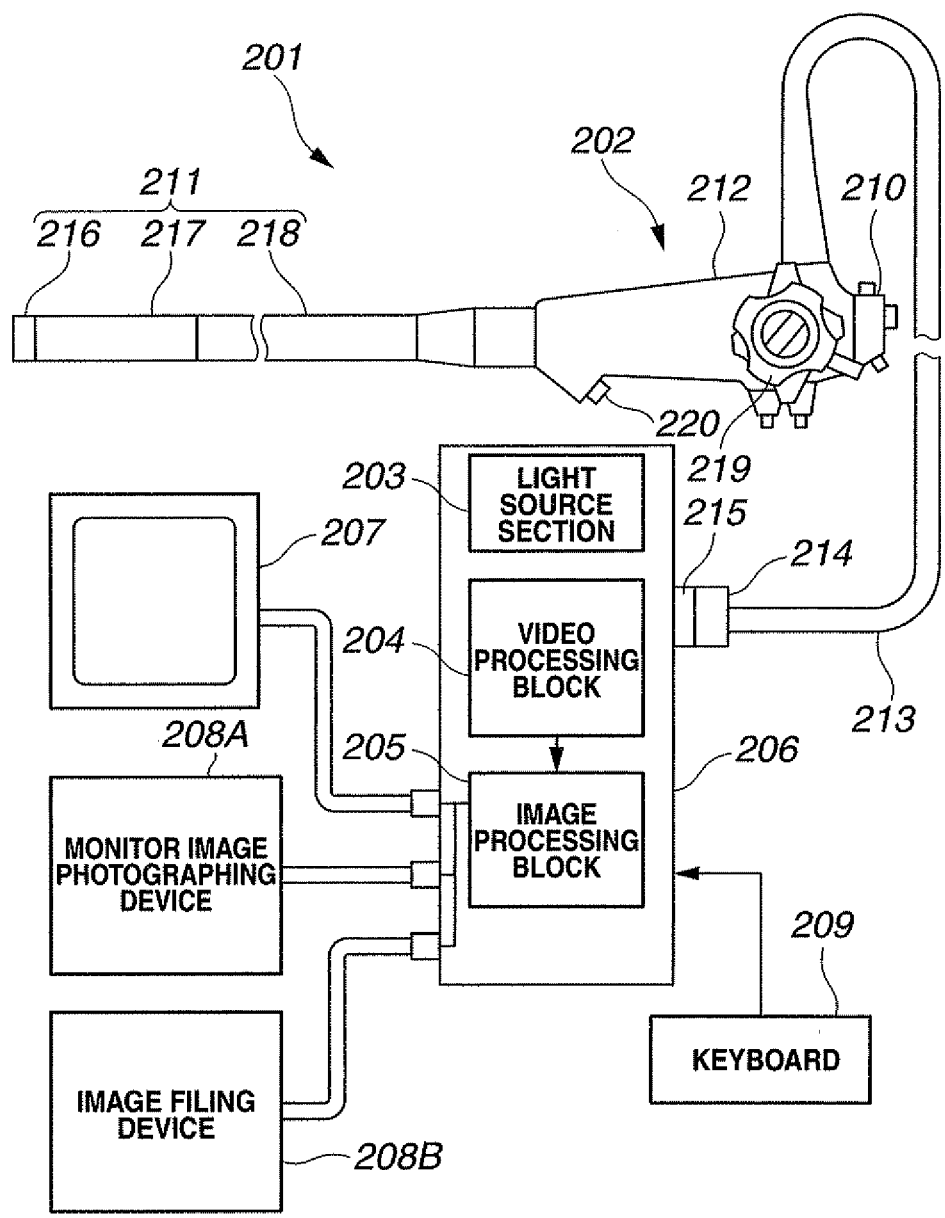
FIG. 33 is a diagram showing a configuration of features of an endoscope apparatus according to a fifth embodiment of the present invention.

Next, a fifth embodiment of the present invention will be described. As shown in FIG. 33, an endoscope apparatus 201 as an image processing apparatus is configured to comprise as substantial components: an electronic endoscope 202 that picks up an image of a subject; a light source section 203 as light source means that supplies illumination light to the electronic endoscope 202; a processor 206; a monitor 207 that displays a picture of the subject based on an image signal outputted from the processor 206; a monitor image photographing device 208A that photographs the picture of the subject displayed on the monitor 207 (hereinafter also referred to as "endoscopic image") as display means; an image filing device 208B connected to the processor 206 and which performs storing of image information and the like; and a keyboard 209 for outputting an instruction signal that cases the processor 206 to perform image processing, inputting patient data, and the like.

In addition, the processor 206 is configured to comprise: a video processing block 204 that performs signal processing on an image pickup signal outputted from the electronic endoscope 202; an image processing block 205 that performs image processing on a signal outputted from the video processing block 204 and outputs the same as an image signal; and an image storing section, not shown, that stores an image signal outputted from the image processing block 205.

The electronic endoscope 202 includes an elongated and, for example, flexible insertion portion 211. A wide operation section 212 is connected to a rear end of the insertion portion 211, and further, a flexible universal cord 213 is extended from a lateral portion of a rear end-side of the operation section 212. In addition, a connector 214 provided at an end portion of the universal cord 213 is configured so as to be detachably connectable to a connector receiving portion 215 of the processor 206.

The insertion portion 211 of the electronic endoscope 202 is provided with, in sequence from a distal end side thereof, a rigid distal end portion 216, a bendable bending portion 217 adjacent to the distal end portion 216, and a flexible and long flexible portion 218.

A bending operation knob 219 provided at the operation section 212 of the electronic endoscope 202 responds to rotational operations by the user, and is configured so as to be capable of bending the bending portion 217 in an up-down direction or a left-right direction. In addition, an insertion slot 220 communicating with a treatment instrument channel, not shown, provided inside the insertion portion 211 is provided at the operation section 212 of the electronic endoscope 202.

A scope switch 210 configured so as to comprise switches including a freeze switch as freeze instructing means that issues freeze instructions, a release switch that issues release instructions, and an observation mode switching switch that issues observation mode switching instructions, is provided on the top of the operation section 212 of the electronic endoscope 202.

Figure 34:
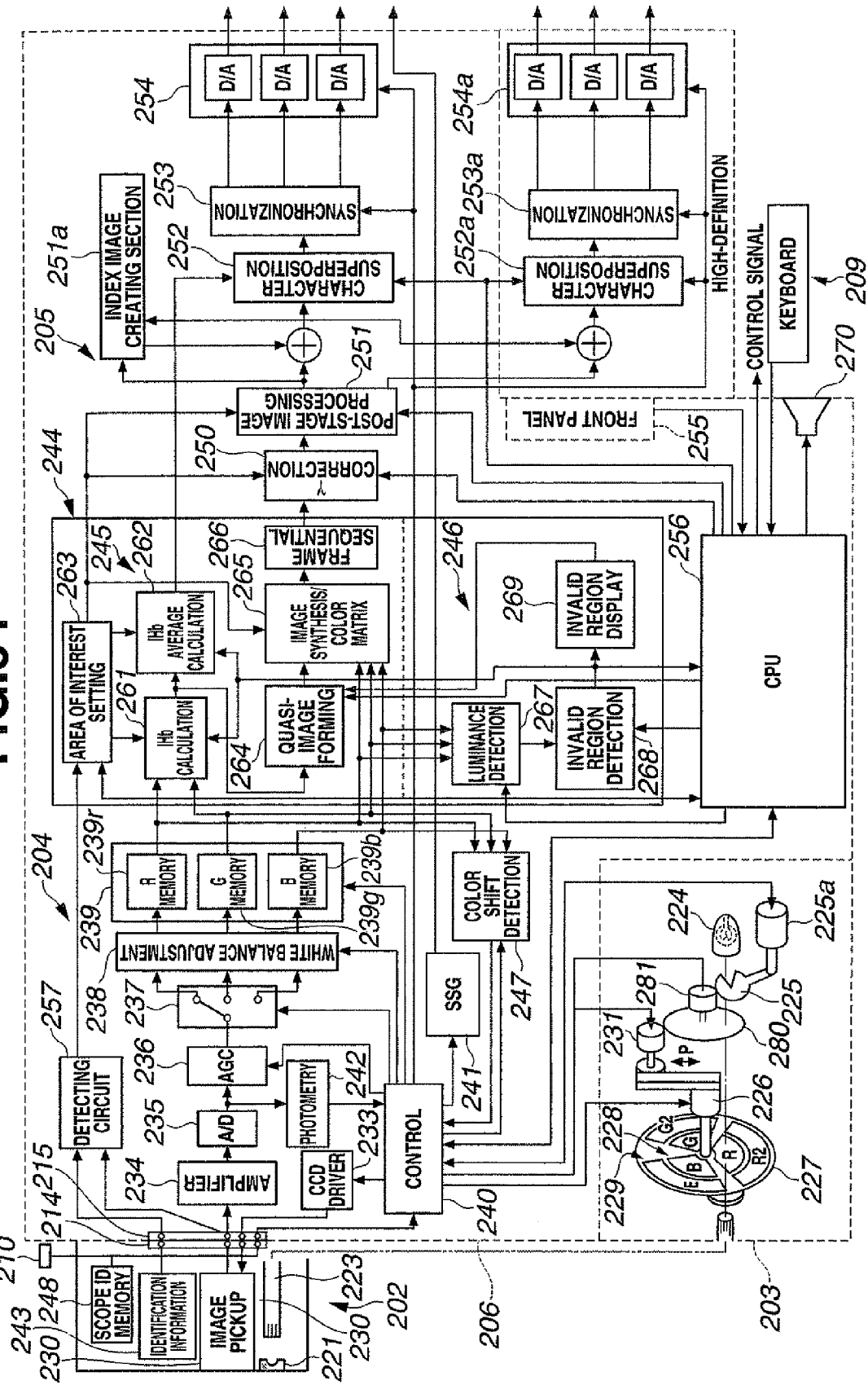
FIG. 34 is a diagram showing an internal configuration of the endoscope apparatus according to the fifth embodiment of the present invention.

For instance, when the scope switch 210 is operated and a freeze instruction is issued, an instruction signal is outputted from the scope switch 210. As shown in FIG. 34, the instruction signal outputted from the scope switch 210 is inputted to a control circuit 240, to be described later, which is provided inside the processor 206. Then, based on the instruction signal outputted from the scope switch 210, the control circuit 240 controls a memory section 239, to be described later, so that a freeze image is displayed.

Upon connection of the electronic endoscope 202 and the processor 206, a scope ID memory 248 provided inside the electronic endoscope 202 outputs information including, for example, observation modes (normal image, autofluorescence observation, Narrow Band Imaging and infrared observation) available for the electronic endoscope 202, adaptive regions (upper digestive tract, lower digestive tract and bronchial tubes) by the electronic endoscope 202, and correction parameters regarding variations in equipment (including differences among models and individual differences) to the control circuit 240 and a CPU 256.

Upon connection of the electronic endoscope 202 and the processor 206, an identification information circuit 243 provided inside the electronic endoscope 202 outputs, for example, information including model information to the control circuit 240 and the CPU 256.

A white balance adjusting circuit 238 provided in the video processing block 204 of the processor 206 performs signal processing for correcting variations in color tones attributable to, for example, variations in equipment such as transmission characteristics of optical systems included in the electronic endoscope 202.

A description will now be given on a storing method of endoscopic images displayed on the monitor 207.

A user causes an instruction signal for issuing a freeze instruction to be outputted to the control circuit 240 by operating the keyboard 209, the front panel 255 of the processor 206 and the like. Based on the instruction signal, the control circuit 240 performs control corresponding to the freeze instruction.

In addition, the user causes an instruction signal for issuing a release instruction to be outputted by operating the keyboard 209, the front panel 255 of the processor 206 and the like. Based on the instruction signal, if a freeze image is not displayed, the CPU 256 performs control for realizing a freeze image display state via the control circuit 240, and at the same time, outputs a control signal based on the release instruction to the monitor image photographing device 208A. Based on the control signal outputted from the CPU 256, the monitor image photographing device 208A performs photographing of the endoscopic image displayed on the monitor 207.

An image processing method will now be described.

The user causes an instruction signal for issuing an image processing instruction to be outputted by operating the keyboard 209, the front panel 255 of the processor 206 and the like. Based on the instruction signal, the CPU 256 performs image processing corresponding to the image processing instruction by controlling an IHb calculating circuit 261, an IHb average calculating circuit 262, a luminance detecting circuit 267, an invalid region detecting circuit 268 and the like of an IHb processing block 244. Incidentally, the user can also suspend image processing performed by the respective parts of the IHb processing block 244 at any time by operating, for example, the keyboard 209, the front panel 255 of the processor 206 and the like.

In addition, the user causes an instruction signal for issuing an observation mode switching instruction to be outputted by operating the scope switch 210 of the electronic endoscope 202. The control circuit 240 performs control over a moving motor 231 and a motor 281, to be described later, based on the instruction signal to move a rotary filter 227 and a band switching filter 280 in order to switch the observation mode from, for example, the normal observation mode to the fluorescence observation mode.

A description will now be given on the electronic endoscope 202 and the light source section 203.

As shown in FIG. 34, the distal end portion 216 of the electronic endoscope 202 is configured to comprise an illuminating lens 221 and an image pickup section 230.

Figure 43:
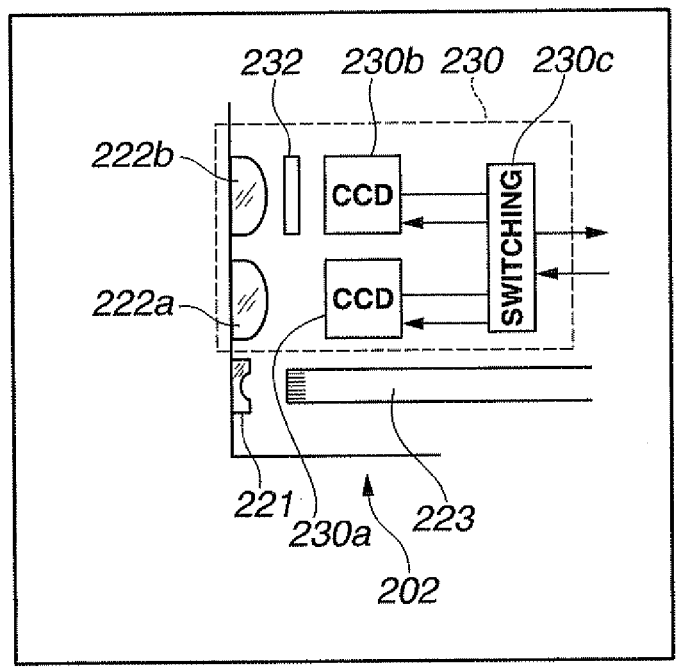
FIG. 43 is a diagram showing an example of a configuration of an image pickup section provided in the electronic endoscope included in the endoscope apparatus according to the fifth embodiment of the present invention.

As shown in FIG. 43, the image pickup section is configured to comprise: objective optical systems 222a and 222b that form pictures of a subject; a CCD 230a as image pickup means provided at an image forming position of the objective optical system 222a and which picks up the subject picture formed by the objective optical system 222a; a CCD 230b as image pickup means provided at an image forming position of the objective optical system 222b, which picks up the subject picture formed by the objective optical system 222b and which is capable of image pickup at a higher sensitivity than the CCD 230a; a switching section 230c that switches driving states of the CCD 230a and the CCD 230b based on a switching signal outputted from the control circuit 240; and an excitation light cutoff filter 232 positioned on a front face of an image pickup plane of the CCD 230b. In addition, the excitation light cutoff filter 232 has a property of cutting off excitation light between 390 nm and 450 nm and extracting fluorescence.

Incidentally, in the present embodiment, it is assumed that the switching section 230c drives the CCD 230a when the observation mode of the endoscope apparatus 201 is switched to the normal observation mode, and drives the CCD 230b when the observation mode of the endoscope apparatus 201 is switched to the fluorescence observation mode.

In addition, an output end that is one end of a light guide 223 constituted by a fiber bundle is positioned on a rear end side of the illuminating lens 221. The light guide 223 is provided so as to be inserted through the insertion portion 211, the operation section 212 and the inside of the universal cord 213, and an incident end that is the other end thereof is positioned inside a connector 214. By configuring the light guide 223 as described above, when the connector 214 is connected to the processor 206, illumination light outputted from the light source section 203 inside the processor 206 enters the incident end of the light guide 223 and is subsequently outputted from the output end positioned on the rear end side of the illuminating lens to illuminate the subject.

The light source section 203 comprises a lamp 224 constituted by, for example, a xenon lamp or the like which outputs illumination light including visible light. Illumination light outputted from the lamp 224 is incident via a diaphragm 225 placed on a light path of the lamp 224 to the rotary filter 227 rotated by a motor 226. Then, illumination light transmitted through and outputted from the rotary filter 227 is collected by a collecting lens, and is incident to the incident end of the light guide 223. In addition, the diaphragm 225 is configured so as to be driven in accordance with the driving state of a diaphragm motor 225a that is controlled by the control circuit 240.

Figure 35:
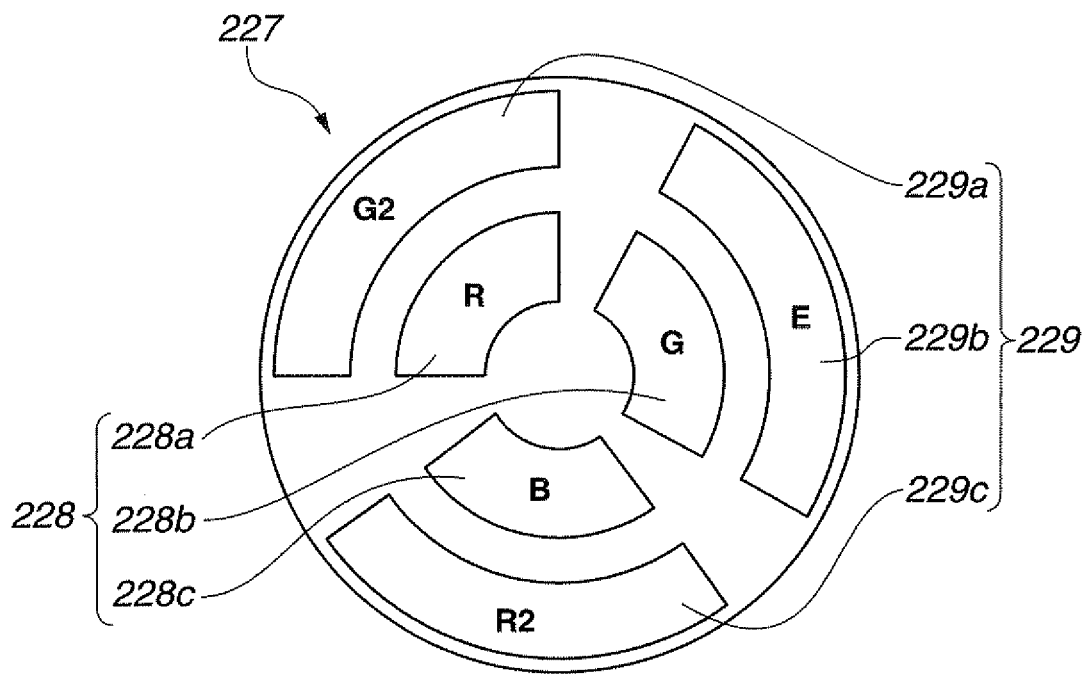
FIG. 35 is a diagram showing a configuration of a rotary filter provided at a light source section included in the endoscope apparatus according to the fifth embodiment of the present invention.

As shown in FIG. 35, the rotary filter 227 is configured so that a normal observation RGB filter 228 is positioned on an inner peripheral side of a concentric pattern and a fluorescence observation filter 229 is positioned on an outer peripheral side of the concentric pattern. In addition, the rotary filter 227 is moved together with the motor 226 for rotating the rotary filter 227 by the moving motor 231 in a direction perpendicular to the light path of the lamp 224, which is the direction indicated by an arrow P in FIG. 34. In other words, when an observation mode switching instruction is issued, the moving motor 231 switches filters positioned on the light path of the lamp 224 by moving the motor 226 and the rotary filter 227. Incidentally, in the present invention, it is assumed that the control circuit 240 outputs to the moving motor 231 a switching signal for performing control so that the RGB filter 228 is positioned on the light path of the lamp 224 when the normal observation mode, the Narrow Band Imaging mode or the infrared observation mode is selected as the observation mode, and that the control circuit 240 outputs to the moving motor 231 a switching signal for performing control so that the fluorescence observation filter 229 is positioned on the light path of the lamp 224 when the fluorescence observation mode is selected as the observation mode.

Figure 36:
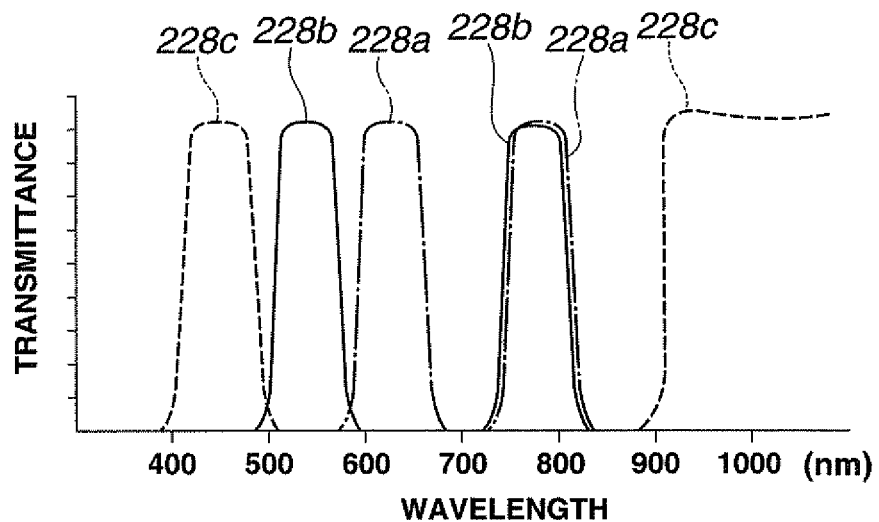
FIG. 36 is a diagram showing transmission characteristics of an RGB filter provided in the rotary filter shown in FIG. 35, according to the fifth embodiment of the present invention.

The RGB filter 228 is configured so as to comprise an R filter 228a, a G filter 228b and a B filter 228c respectively having transmission characteristics shown in FIG. 36. More specifically, the R filter 228a is configured to transmit a red wavelength band of 600 nm to 700 nm, the G filter 228b is configured to transmit a green wavelength band of 500 nm to 600 nm, and the B filter 228c is configured to transmit a blue wavelength band of 400 nm to 500 mm.

Furthermore, in addition to the above-described configurations, the R filter 228a and the G filter 228b are configured to transmit a wavelength band of 790 nm to 820 nm for infrared observation. Moreover, in addition to the above-described configuration, the B filter 228c is configured to transmit a wavelength band of 900 nm to 980 nm for infrared observation. Consequently, during the normal observation mode, by performing processing such as synthesis on an image pickup signal based on a subject picture picked up under an illumination light transmitted through the R filter 228a, a subject picture picked up under an illumination light transmitted through the G filter 228b and a subject picture picked up under an illumination light transmitted through the B filter 228c, the processor 206 creates, as a subject picture, an observation image for normal observation which is an image that shows a picture that is approximately the same as a picture of the subject observed by the naked eye.

Figure 37:
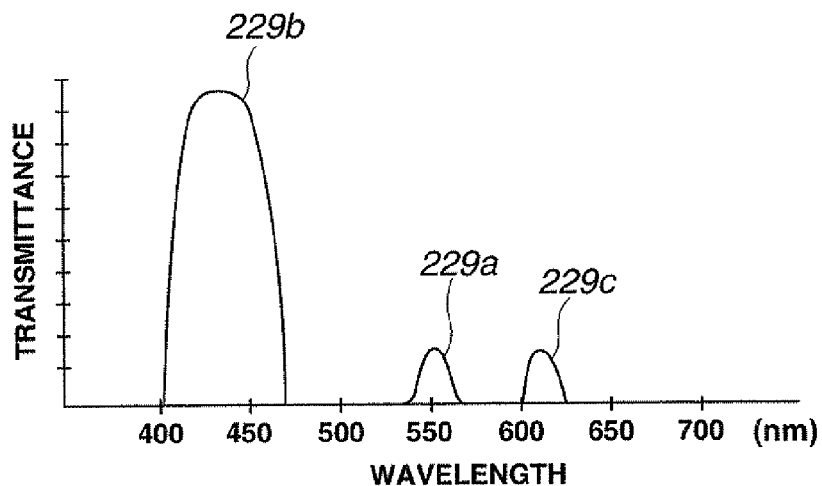
FIG. 37 is a diagram showing transmission characteristics of a fluorescence observation filter provided in the rotary filter shown in FIG. 35, according to the fifth embodiment of the present invention.

The fluorescence observation filter 229 is configured so as to comprise a G2 filter 229a, an E filter 229b and an R2 filter 229c respectively having transmission characteristics shown in FIG. 37. More specifically, the G2 filter 229a is configured to transmit a wavelength band of 540 nm to 560 nm, the E filter 229b is configured to transmit green wavelength band of 400 nm to 470 nm, and the R2 filter 229c is configured to transmit a wavelength band of 600 nm to 620 nm.

Incidentally, as shown in FIG. 37, the transmittances of the G2 filter 229a and the R2 filter 229c are set lower than the transmittance of the E filter 229b. Consequently, during the fluorescence observation mode, by performing processing such as synthesis on an image pickup signal based on a subject picture picked up under an illumination light transmitted through the G2 filter 229a (hereinafter abbreviated as G2 signal), a subject picture picked up under an illumination light transmitted through the R2 filter 229c (hereinafter abbreviated as R2 signal) and a fluorescence signal that is an image pickup signal based on a fluorescence picture emitted by the subject, the processor 206 creates, as a subject picture, an observation image for fluorescence observation which is an quasi-colorized image of the fluorescence picture emitted by the subject.

Figure 38:
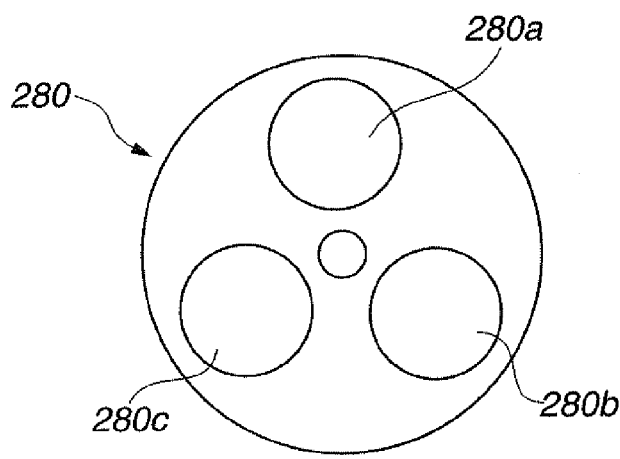
FIG. 38 is a diagram showing a configuration of a band switching filter provided at a light source section included in the endoscope apparatus according to the fifth embodiment of the present invention.

As shown in FIG. 38, the band switching filter 280 is configured to comprise a normal/fluorescence observation filter 280a, a Narrow Band Imaging filter 280b, and an infrared observation filter 280c. The normal/fluorescence observation filter 280a and the infrared observation filter 280c are configured so as to have transmission characteristics shown in FIG. 39. In addition, as shown in FIG. 40, the Narrow Band Imaging filter 280b is constituted by a trimodal filter that transmits, as a single filter, three discrete bands.

The excitation light cutoff filter 232 of the electronic endoscope 202 is configured so as to have a transmission characteristic such as that shown in FIG. 41 so that a transmitted band thereof does not overlap with the transmission characteristic of the E filter 229b shown in FIG. 37.

The band switching filter 280 is rotationally driven by the motor 281 according to a filter switching instructing signal from the CPU 256. In addition, due to rotational driving from the motor 281, the band switching filter 280 is configured so that: the normal/fluorescence observation filter 280a is positioned on the light path of the lamp 224 when normal observation and fluorescence observation are performed; the Narrow Band Imaging filter 280b is positioned on the light path of the lamp 224 when Narrow Band Imaging is performed; and the infrared observation filter 280c is positioned on the light path of the lamp 224 when infrared observation is performed.

Due to the combination of the rotary filter 227 and the band switching filter 280 that are positioned on the light path of the lamp 224, when normal observation is performed, lights having red, green and blue bands are sequentially outputted from the light source section 203. In addition, when Narrow Band Imaging is performed, depending on the combination of transmission characteristics shown in FIG. 36 and transmission characteristics shown in FIG. 40, lights having bands of 600 nm to 630 nm, 530 nm to 660 nm, and 400 nm to 430 nm are sequentially outputted from the light source section 203.

Figure 39:
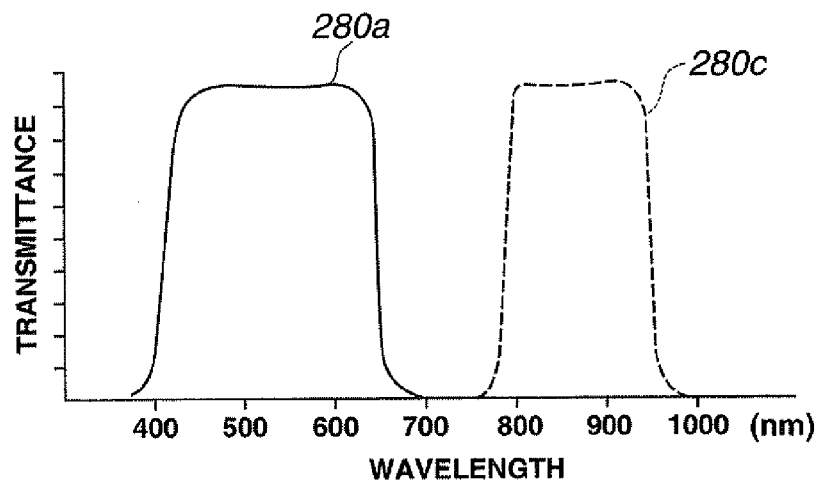
FIG. 39 is a diagram showing transmission characteristics of a normal/fluorescence observation filter and an infrared observation filter provided in the band switching filter shown in FIG. 38, according to the fifth embodiment of the present invention.

On the other hand, when infrared observation is performed, due to the combination of transmission characteristics shown in FIG. 36 and transmission characteristics shown in FIG. 39, lights having bands of 790 nm to 820 nm, 790 nm to 820 nm, and 900 nm to 980 nm are sequentially outputted from the light source section 203.

Furthermore, when fluorescence observation is performed, due to the combination of transmission characteristics shown in FIG. 37 and transmission characteristics shown in FIG. 39, lights having bands of 540 nm to 560 nm, 390 nm to 450 nm, and 600 nm to 620 nm are sequentially outputted from the light source section 203. Incidentally, light having a band of 390 nm to 450 nm is an excitation light for exciting autofluorescence from living tissue.

Illumination light incident to the light guide 223 of the electronic endoscope 202 is irradiated from the distal end portion 216 of the electronic endoscope 202 to a subject such as living tissue. Light scattered, reflected and radiated at the subject is used for image forming and image pickup at an image pickup section 230 provided at the distal end portion 216 of the electronic endoscope 202.

Moreover, illumination light incident to the light guide 223 of the electronic endoscope 202 is guided by the light guide 223 to the distal end portion 216, and then passed through the illuminating lens 221 attached to an irradiating window on a distal end face and irradiated to the subject. In this case, under the normal observation mode, a frame sequential illumination light of R (red), G (green) and B (blue) is realized. In addition, under the fluorescence observation mode, a frame sequential illumination light of G2, E and R2 is realized.

The CCDs 230a and 230b are respectively driven in synchronization with the rotation of the rotary filter 227 when a CCD driving signal is applied from a CCD driver 233. In addition, the CCDs 230a and 230b respectively perform photoelectric conversion on pictures respectively formed by the objective optical systems 222a and 222b, and outputs the same as image pickup signals. As a result, image pickup signals respectively corresponding to illumination lights transmitted through the RGB filter 228 and the fluorescence observation filter 229 of the rotary filter 227 are outputted to the processor 206.

Incidentally, by controlling the CCD driver 233, the control circuit 240 or the CPU 256 can be arranged to act as an electronic shutter that variably controls the charge accumulation times by the CCDs 230a and 230b.

A description will now be given on the processor 206.

Time-series image pickup signals outputted from the CCDs 230a and 230b are first inputted to an amplifier 234 provided inside the video processing block 204, and then amplified to a predetermined signal level such as 0 to 1 volt.

In this case, the time-series image pickup signals become respective color signals of R, G and B under the normal observation mode and become a G2 signal, a fluorescence signal and an R2 signal under the fluorescence observation mode. Incidentally, during The Narrow Band Imaging mode and the infrared observation mode, signals corresponding to the respective illumination lights are obtained.

An image pickup signal outputted from the amplifier 234 is converted into a digital signal at an A/D converter 235, and then outputted to an automatic gain control circuit (hereinafter abbreviated as AGC circuit) 236. Subsequently, the AGC circuit 236 controls the gain of the image pickup signal outputted from the A/D converter 235 so that an appropriate signal level is attained before outputting the signal.

The image pickup signal outputted from the AGC circuit 236 is inputted to a one-input three-output selector 237. For image pickup signals sent in a time-series, the selector 237 switches the respective color signals of R, G and B or G2, fluorescence and R2 signals, and sequentially inputs the signals to a white balance adjusting circuit 238. At the white balance adjusting circuit 238, when an image of a white subject to be used as a reference is picked up, gain is adjusted or, in other words, white balance adjustment is performed so that the signal levels of the respective color signals of R, G and B become equal. Subsequently, an image pickup signal outputted from the white balance adjusting circuit 238 is inputted to a memory section 239 that constitutes a portion of freeze image creating means and which is storing means. Incidentally, white balance adjustment may instead be automatically performed by reading a white balance adjustment value from the scope ID memory 248 provided at the electronic endoscope 202.

Furthermore, image pickup signals inputted in a time-series such as the respective color signals of R, G and B are respectively stored in R, G and D memories 239r, 239g and 239b which constitute the memory section 239.

By configuring the memory section 239 as described above, during the normal observation mode, an R color signal is stored in the R memory 239r, a G color signal is stored in the G memory 239g, and a B color signal is stored in the B memory 239b. In addition, during the fluorescence observation mode, a G2 signal is stored in the R memory 239r, a fluorescence signal is stored in the G memory 239g, and an R2 signal is stored in the B memory 239b.

A/D conversion by the A/D converter 235, switching by the selector 237, control during white balance adjustment, as well as write and read of image pickup signals such as the respective color signals of R, G and B to/from the R, G and B memories 239r, 239g and 239b are controlled by the control circuit 240. In other words, an image pickup signal outputted from the white balance adjusting circuit 238 is written into the memory section 239 based on a write signal outputted by the control circuit 240 to the memory section 239. Additionally, the image pickup signal written into the memory section 239 is read out therefrom based on a read signal outputted by the control circuit 240 to the memory section 239.

Furthermore, the control circuit 240 sends a reference signal to a synchronizing signal generating circuit (abbreviated in FIG. 34 as SSG) 241. The synchronizing signal generating circuit 241 generates a synchronizing signal that is synchronized with the reference signal. A still image is displayed on the monitor 207 as a result of the control circuit 240 performing write inhibition control over the R, G and B memories 239r, 239g and 239b. Write inhibition control over the R, G and B memories 239r, 239g and 239b can also be performed at the synchronizing circuit 253.

In addition, an image pickup signal outputted from the A/D converter 235 is metered at the photometric circuit 242 and then inputted to the control circuit 240.

The control circuit 240 compares an average obtained by integrating signals metered at the photometric circuit 242 to an reference value in a case of appropriate brightness, and drives the diaphragm motor 225a by outputting a modulated light signal based on the comparison result. The control circuit 240 adjusts the light quantity of illumination light outputted from the light source section 203 so as to reduce the difference between the average and the reference value by controlling the aperture of the diaphragm 225 driven in conjunction with the diaphragm motor 225a.

A rotary encoder or the like, not shown, for detecting a diaphragm position corresponding to the aperture of the diaphragm 225 is mounted on the diaphragm motor 225a. A detection signal of the rotary encoder is inputted to the control circuit 240. Consequently, the control circuit 240 is able to detect a position of the diaphragm 225 from a detection signal outputted from the rotary encoder. In addition, the control circuit 240 is connected to the CPU 256. Therefore, the CPU 256 is able to confirm the position of the diaphragm 225 detected at the control circuit 240.

Image processing enabled in the normal observation mode will now be described.

In the case of the normal observation mode, the respective color signals of R, G and B read from the R, G and B memories 239r, 239g and 239b are inputted to the IHb processing block 244 constituting the image processing block 205 and which performs processing such as calculation of a value correlated with a hemoglobin content (hereinafter abbreviated as IHb) as a pigment content to be used as a blood information content.

In the present embodiment, for example, the IHb processing block 244 calculates an IHb value of each pixel within an area of interest set in a setting screen of the processor 206 such as that shown in FIG. 42, and is configured to comprise: an IHb processing circuit section 245 that performs quasi-image creation processing for displaying as a quasi-color image an IHb image that is an image displayed based on the IHb value; and an invalid region detecting circuit 246 that detects an invalid region not suitable for image processing with respect to the set area of interest. More specifically, the IHb calculating circuit 261 calculates an IHb value of each pixel by performing computation based on formula (1) below.

$$IHb = 32 \times \log 2(R/G) \quad (1)$$

where R denotes data of R images within the area of interest excluding the invalid region, and G denotes data of G images within the area of interest excluding the invalid region.

A signal outputted from the IHb processing block 244 is subjected to γ correction at a γ correcting circuit 250 and outputted therefrom, and subsequently subjected to structure emphasis at a post-stage image processing circuit 251 and outputted therefrom. The signal outputted from the post-stage image processing circuit 251 is superimposed at a character superimposing circuit 252 with data related to a patient possessing a living tissue or the like to be used as a subject and with the IHb average calculated at the IHb processing block 244, and subsequently synchronized at the synchronizing circuit 253. The synchronizing circuit 253 internally includes three frame memories, not shown, and by sequentially writing frame sequential signal data into the frame memories while simultaneously reading frame sequential signals, outputs a signal such as an RGB signal.

The signals synchronized by the synchronizing circuit 253 are respectively inputted to three D/A converters provided at a D/A converting section 254 to be converted into analog RGB signals or the like, and then respectively outputted to the monitor 207, the monitor image photographing device 208A and the image filing device 208B.

Incidentally, separately from the character superimposing circuit 252, the synchronizing circuit 253 and the D/A converting section 254 described above, the processor 206 comprises: a character superimposing circuit 252a having a configuration that is approximately the same as the character superimposing circuit 252, a synchronizing circuit 253a having a configuration that is approximately the same as the synchronizing circuit 253 and a D/A converting section 254a having a configuration that is approximately the same as the D/A converting section 254 for performing processing to output high-definition images.

An index image creating section 251a performs processing based on signals outputted from the post-stage image processing circuit 251, and outputs the post-processing signals to the character superimposing circuit 252.

A detecting circuit 257 performs processing based on the signals outputted from the image pickup section 230 and the identification information circuit 243, and outputs the post-processing signals to an area of interest setting circuit 263.

The area of interest setting circuit 263 performs processing based on the signals outputted from the CPU 256 and the detecting circuit 257, and outputs the post-processing signals to the γ correcting circuit 250, the post-stage image processing circuit 251, the IHb calculating circuit 261, the IHb average calculating circuit 262 and an image synthesizing/color matrix circuit 265.

A quasi-image forming circuit 264 performs processing based on the signals outputted from the CPU 256, the IHb calculating circuit 261 and an invalid region displaying circuit 269, and outputs the post-processing signals to the image synthesizing/color matrix circuit 265.

The invalid region displaying circuit 269 performs processing based on the signals outputted from the CPU 256 and the invalid region detecting circuit 268, and outputs the post-processing signals to the quasi-image forming circuit 264.

A speaker 270 performs, for example, notification on the status of the processor 206 by playing a predetermined sound based on the control by the CPU 256.

Incidentally, write and read of the frame memories inside the synchronizing circuit 253 and D/A conversion by the D/A converting section 254 are controlled by the control circuit 240. In addition, the CPU 256 controls operations of the γ correcting circuit 250, the post-stage image processing circuit 251 and the character superimposing circuit 252.

The monitor image photographing device 208A is configured to comprise: a monitor, not shown, having a configuration that is approximately the same as the monitor 207 and which displays images and the like; and a photographing device, not shown, that is a camera or the like which performs image storing of images or the like displayed on the monitor through photographing.

By operating a switch, not shown, provided on the front panel 255 of the processor 206 or by operating the keyboard 209, the user can output instructing signals to the CPU 256 for instructing a subject picture picked up in the normal observation mode to be displayed on the monitor 207 or instructing an IHb image to be displayed on the monitor 207. Based on the instructing signal outputted through an operation of the switch, not shown, provided on the front panel 255 of the processor 206 or an operation of the keyboard 209, the CPU 256 performs control over the IHb processing block 244 and the like.

Image processing enabled in the respective observation modes other than the normal observation mode will now be described.

In a case where the respective parts of the endoscope apparatus 201 are set to the fluorescence observation mode, the CCD 230b is driven while driving of the CCD 230a is suspended. Consequently, the CCD 230b is able to pick up pictures under autofluorescence emitted from a subject in the fluorescence observation mode. In addition, at a timing that is approximately the same as the timing where switching is performed from one observation mode other than the fluorescence observation mode to the fluorescence observation mode, the light source section 203 sets the rotation speed of the rotary filter 227 to half of that in the observation mode. As a result, the CCD 230b picks up a picture under autofluorescence emitted from the subject over a longer exposure time than that in the observation mode other than the fluorescence observation mode, and outputs the picked up autofluorescence picture as an image pickup signal.

In addition, in the fluorescence observation mode, with the respective color signals of R, G and B written into the R, G and B memories 239r, 239g and 239b, for example, same signals are read twice from the respective R, G and B memories 239r, 239g and 239b in accordance with the exposure time during the fluorescence observation mode.

Read out G2, fluorescence and R2 signals are outputted to the post-stage image processing circuit 251 via the image synthesizing/color matrix circuit 265, a frame sequential circuit 266 and the like. Subsequently, the post-stage image processing circuit 251 uses a color matrix to perform processing so that for example, the G2 signal is quasi-color displayed on the monitor 207 as red, the fluorescence signal as green, and the R2 signal having its signal level multiplied by 0.5 as blue.

Incidentally, in a case where the respective parts of the endoscope apparatus 201 are set to the Narrow Band Imaging mode or the infrared observation mode, the CCD 230a is driven while driving of the CCD 230b is suspended. In addition, in the case where the respective parts of the endoscope apparatus 201 are set to the Narrow Band Imaging mode or the infrared observation mode, exposure is performed over an exposure time that is approximately the same as the exposure time during the normal observation mode. Therefore, the CCD 230a picks up a subject picture over an exposure time that is approximately the same as the exposure time during the normal observation mode and outputs the picked up subject picture as an image pickup signal. In addition, in a case where the respective parts of the endoscope apparatus 201 are set to the Narrow Band Imaging mode or the infrared observation mode, the subject image is color-displayed on the monitor 207 by the respective color signals and the color matrix.

A description will now be given on a case where the observation mode of the endoscope apparatus 201 is switched from one observation mode to another observation mode.

For the following description, it is assumed that the afore-mentioned observation mode is the normal observation mode and the afore-mentioned other observation mode is the fluorescence observation mode.

Figure 45:
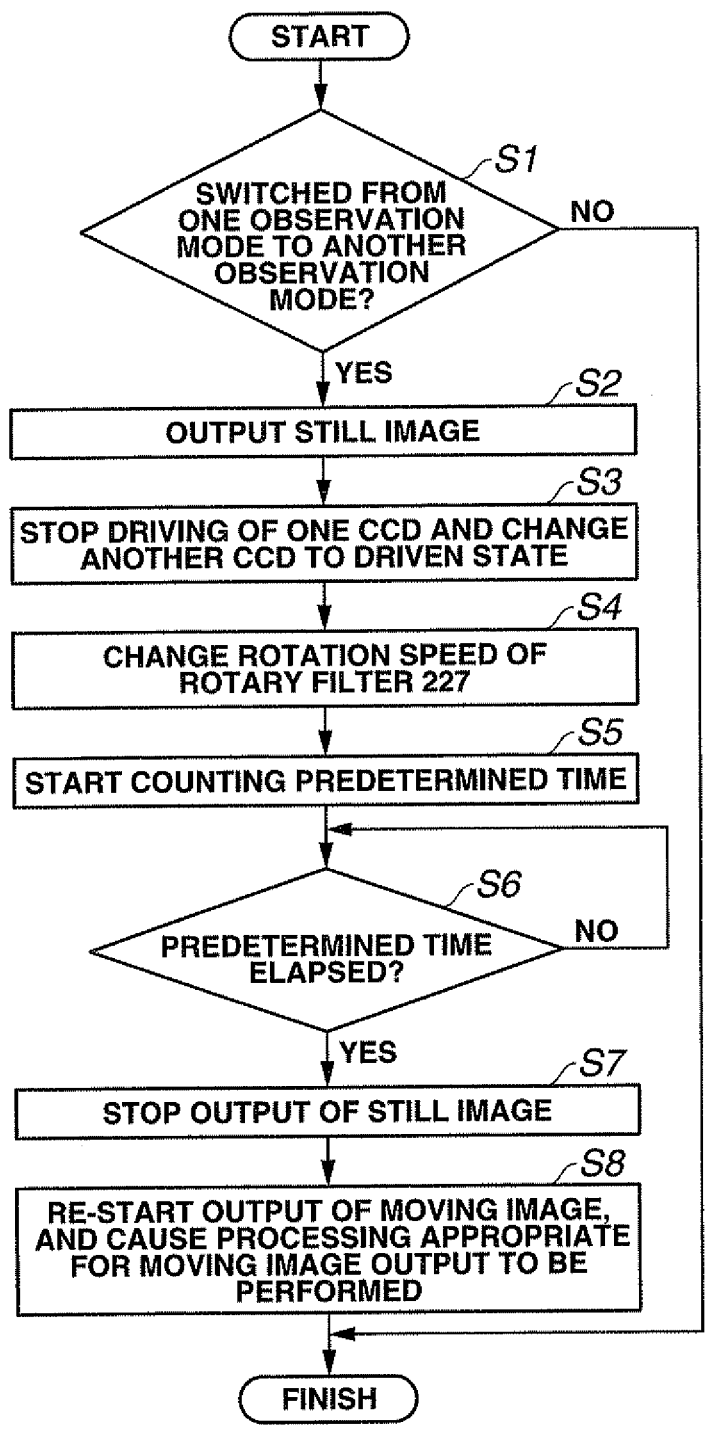
FIG. 45 is a flowchart showing an example of processing performed at the processor when the observation mode of the endoscope apparatus is switched from one observation mode to another observation mode according to the fifth embodiment of the present invention.

Prior to performing the processing represented by step S1 in FIG. 45, the control circuit 240 outputs a write signal to the memory section 239. Image pickup signals are writable to the memory section 239 in a state where a write signal outputted from the control circuit 240 is being inputted.

In the processing represented by step S1 in FIG. 45, when the control circuit 240 detects that switching has been performed from the normal observation mode to the fluorescence observation mode, the control circuit 240 performs control so as to cause a still image to be created and outputted by outputting a switching signal to the synchronizing circuit 253 in the processing represented by step S2 in FIG. 45.

Subsequently, in the processing represented by step S3 in FIG. 45, the control circuit 240 outputs a switching signal to the switching section 230c of the image pickup section 230 to perform control that causes the CCD 230b, as one CCD, to be driven and causes driving of the CCD 230a, as another CCD, to be suspended. Then, based on the switching signal outputted from the control circuit 240, the switching section 230c switches the driving states of the CCDs 230a and 230b. Furthermore, the control circuit 240 performs the above-described processing represented by step S3 in FIG. 45, and at the same time suspends output of the write signal to the memory section 239. Consequently, the memory section 239 suspends writing of an image pickup signal at the timing at which input of the write signal outputted from the control circuit 240 is suspended. In addition, in the processing represented by step S4 in FIG. 45, the control circuit 240 changes the rotation speed of the rotary filter 227 to, for example, a rotation speed that is half of the normal observation mode.

In the processing represented by steps S5 and S6 in FIG. 45, the control circuit 240 performs counting of a predetermined time period. Incidentally, in a case where switching is performed from the normal observation mode to the fluorescence observation mode, it is assumed that the predetermined time period is, for example, three seconds.

When the control circuit 240 detects that the predetermined time period has elapsed, the control circuit 240 restarts output of the write signal to the memory section 239, and at the same time, in the processing represented by step S7 in FIG. 45, performs control so as to suspend output of the still image by outputting a switching completion signal to the synchronizing circuit 253. Consequently, the memory section 239 releases suspension of the writing of image pickup signals at the timing at which input of the write signal outputted from the control circuit 240 is restarted.

Subsequently, in the processing represented by step S8 in FIG. 45, the control circuit 240 causes the synchronizing circuit 253 to restart output of a moving image, and, at the same time, causes the post-stage image processing circuit 251 as displayed image size changing means to perform processing appropriate for outputting a moving image such as changing of the size of images to be displayed on the monitor 207 and adjusting of a masking size.

In addition, the processing performed by the post-stage image processing circuit 251 for changing image sizes can be set so that the image size displayed on the monitor 207 is a desired size by, for example, changing "fluorescence observation display size" in the setting screen of the processor 206 shown in FIG. 42.

Processing for creating a still image and switching moving images performed by the synchronizing circuit 253 will now be described.

During time series numbers 1 to 4 shown in FIG. 50 or, in other words, during the normal observation mode, the synchronizing circuit 253 sequentially writes an image pickup signal configured to include the respective color signals of R, G and B into three internally provided frame memories, not shown, and outputs a synchronized RGB signal by simultaneously reading out the written image pickup signal.

Then, for example, in a case where a switching signal outputted from the control circuit 240 is inputted at the timing of time series number 4 shown in FIG. 50 when the processing represented by step S2 in FIG. 45 is performed or, in other words, in a case where switching from the normal observation mode to the fluorescence observation mode is performed, the synchronizing circuit 253 suspends writing of the image pickup signal to the three frame memories and, at the same time, creates and outputs a still image at a timing represented by the time series number 4 shown in FIG. 50 at which the switching signal outputted from the control signal is inputted.

In addition, when a switching signal is outputted to the synchronizing circuit 253 at the timing represented by the time series number 4 shown in FIG. 50, the control circuit 240 commences processing represented by step S3 and thereafter in FIG. 45 at a timing represented by the time series number 5 shown in FIG. 50. In accordance with the above-described operation of the control circuit 240, for example, between the time series numbers 5 to 10 shown in FIG. 50 or, in other words, during a time period until a switching completion signal is outputted from the control circuit 240, the synchronizing circuit 253 continues suspension of writing of the image pickup signal to the three frame memories, not shown, and, at the same time, continues outputting the still image created at the timing represented by the time series number 4 shown in FIG. 50.

Subsequently, when a switching completion signal is outputted to the synchronizing circuit 253 at a timing represented by the time series number 11 shown in FIG. 50, the control circuit 240 commences processing represented by step S7 and thereafter in FIG. 45 at, for example, the timing represented by the time series number 11 shown in FIG. 50. Based on the switching completion signal outputted from the control circuit 240, the synchronizing circuit 253 releases suspension of writing of the image pickup signal to the three frame memories, not shown, at the timing represented by the time series number 11 shown in FIG. 50 or, in other words, the timing at which the switching completion signal from the control circuit 240 is inputted and, at the same times suspends output of the still image created at the timing represented by the time series number 4 shown in FIG. 50. The synchronizing circuit 253 then sequentially writes an image pickup signal configured to include a G2 signal, a fluorescence signal and an R2 signal into three internally provided frame memories, not shown, as synchronizing memories, and then outputs a synchronized signal by simultaneously reading out the written image pickup signal. As a result an autofluorescence picture is displayed as a moving image on the monitor 207.

Incidentally, the synchronizing circuit 253 is not limited to an arrangement in which suspension of writing of the image pickup signal to the three frame memories, not shown, is released at a timing at which the switching completion signal from the control circuit 240 is inputted. For example, the synchronizing circuit 253 may be arranged to release suspension of writing of the image pickup signal to the three frame memories, not shown, at a predetermined timing suitable for an observation mode such as the fluorescence observation mode after the switching completion signal from the control circuit 240 is inputted.

As described earlier, by arranging processing for displaying a still image on the monitor 207 to be performed when switching from one observation mode to another observation mode is performed, for example, it is now possible to prevent noise that occurs when one of the CCDs provided at the image pickup section 230 is switched to another CCD thereof and to prevent color changes until the rotation speed of the rotary filter 227 changes to a predetermined rotation speed. As a result, the processor 206 according to the present embodiment is able to output a still image suitable for storing when switching from one observation mode to another observation mode is being performed.

Incidentally, when the observation mode is the fluorescence observation mode and the other observation mode is the normal observation mode, it is assumed that, in the processing represented by step S3 in FIG. 45, the control circuit 240 performs control so as to cause the switching section 230*c* of the image pickup section 230 to drive the CCD 230*a*, as one CCD, and to suspend driving of the CCD 230*b*, as another CCD. In addition, when switching from the fluorescence observation mode to the normal observation mode is performed, in the processing represented by step S4 in FIG. 45, the control circuit 240 changes the rotation speed of the rotary filter 227 to, for example, twice the speed. Furthermore, for the predetermined time in the processing represented by steps S5 and S6 in FIG. 45, it is assumed that counting of, for example, 1.5 seconds is performed.

Incidentally, the synchronizing circuit 253 that constitutes a part of freeze image creating means and which is storing means is configured so as to create and output images of an odd field and an even field in order to display an image on the monitor 207. In addition, there are cases where a still image outputted from the synchronizing circuit 253 in the processing represented by step S2 in FIG. 45 is outputted in a state where a misalignment has occurred between images of an odd field and an even field. In a case such as described above, for example, the synchronizing circuit 253 is able to create and output a still image with few misalignments by having the memory section 239 perform processing for creating a still image in advance before performing the processing represented by step S2 in FIG. 45. The still image created at the memory section 239 by the above-described processing performed by the synchronizing circuit 253 may either be an image when an ordinary freeze instruction is issued or an image immediately prior to switching to the fluorescence observation mode.

In addition, the still image outputted from the synchronizing circuit 253 in the processing represented by step S2 in FIG. 45 may be an image in an odd field adopted to an image in an even field.

Figure 44:
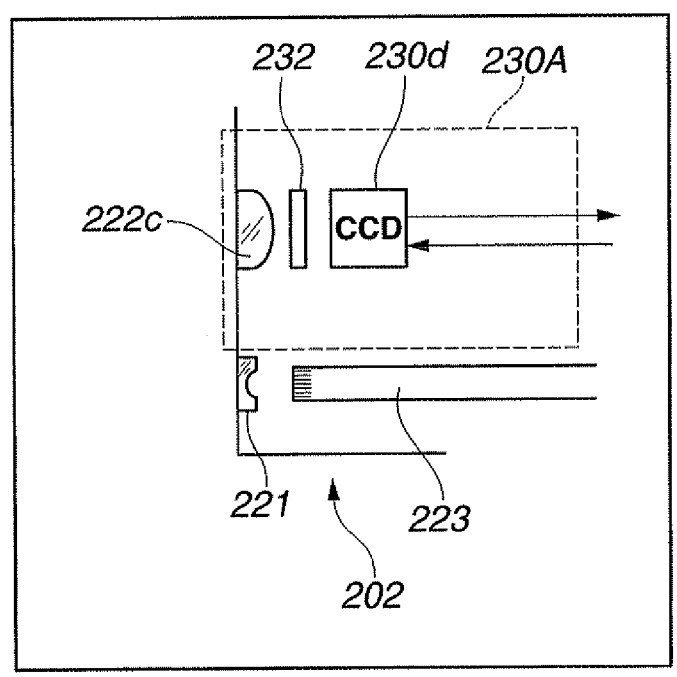
FIG. 44 is a diagram showing an example, which differs from that of FIG. 43, of a configuration of the image pickup section provided in the electronic endoscope included in the endoscope apparatus according to the fifth embodiment of the present invention.

Applications of the above-described processing shown in FIG. 45 is not limited to a case where the electronic endoscope 202 comprises the image pickup section 230 provided with two CCDs such as shown in FIG. 43, and may instead be applied to a case where the electronic endoscope 202 comprises an image pickup section 230A provided with a single CCD as shown in FIG. 44.

Incidentally, as shown in FIG. 44, the image pickup section 230A is configured to comprise: an objective optical system 222c that forms a subject picture; a CCD 230d as image pickup means having approximately the same sensitivity as the CCD 230b, which is provided at an image-forming position of the objective optical system 222c and which picks up the subject picture formed by the objective optical system 222c; and an excitation light cutoff filter 232 positioned on a front face of an image pickup plane of the CCD 230d. In addition, in the case where the electronic endoscope 202 is configured to comprise the image pickup section 230A, it is assumed that the control circuit 240 does not perform the processing represented by step S3 in FIG. 45. Furthermore, in the case where the electronic endoscope 202 is configured to comprise the image pickup section 230A, it is assumed that the control circuit 240 causes the synchronizing circuit 253 to restart output of a moving image without performing processing for adjusting image size and masking size in the processing represented by step S8 in FIG. 45.

Now, a description will be further given on processing performed by the processor 206 in a case where a freeze instruction is issued by the scope switch 210 or the like immediately after the observation mode of the endoscope apparatus 201 is switched from one observation mode to another observation mode.

Image pickup signals outputted from the image pickup section 230 are written in a time series into the memory section 239 in accordance to the rotation speed of the rotary filter 227. When a freeze instruction is issued by the scope switch 210 or the like immediately after the observation mode of the endoscope apparatus 201 is switched from one observation mode to another observation mode, after an image pickup signal having the fewest color shifts among the image pickup signals written into the memory section 239 is detected, a color shift detecting circuit 247 performs processing that causes a still image based on the image pickup signal to be displayed as a freeze image on the monitor 207 or, in other words, performs pre-freeze processing.

More specifically, for example, as shown in FIG. 46, when a freeze instruction is issued at a timing F2 or, in other words, the timing represented by the time series number 21, the color shift detecting circuit 247 detects an image pickup signal having the fewest color shifts among the image pickup signals written into the memory section 239 between the time series numbers 13 to 20, and then performs pre-freeze processing so as to cause a still image based on the image pickup signal to be displayed as a freeze image on the monitor 207.

In addition, for example, when a freeze instruction is issued at a timing F1 or, in other words, the timing represented by the time series number 12 at which the observation mode of the endoscope apparatus 201 is switched from one observation mode to another observation mode, the color shift detecting circuit 247 disables the freeze instruction and, at the same time, does not perform pre-freeze processing. More specifically, even if a freeze instruction is issued at a timing between the time series numbers 5 to 18 as shown in FIG. 46, the color shift detecting circuit 247 disables the freeze instruction and, at the same time, does not perform pre-freeze processing for causing the freeze image to be displayed on the monitor 207.

By having the color shift detecting circuit 247 that constitutes a part of freeze image creating means and which is color shift detecting means perform processing as described above, for example, any of a still image based on image pickup signals written into the memory section 239 between the time series numbers 5 to 10 and which has a high probability of an occurrence of noise as indicated by the Δ in FIG. 46 or a still image based on image pickup signals written into the memory section 239 at a timing represented by the time series number 4 at which switching of CCDs by the image pickup section 230 has not yet been concluded will not be displayed as a freeze image on the monitor 207. As a result, in a case where a freeze instruction is issued immediately after switching from one observation mode to another observation mode is performed, the processor 206 according to the present embodiment is able to prevent output of an image unsuitable for still image storing by disabling the freeze instruction.

Incidentally, the color shift detecting circuit 247 is not limited to an arrangement where the time period in which the freeze instruction is disabled is determined based on time series numbers, and the time period may be determined based on a predetermined time instead.

Figure 48:
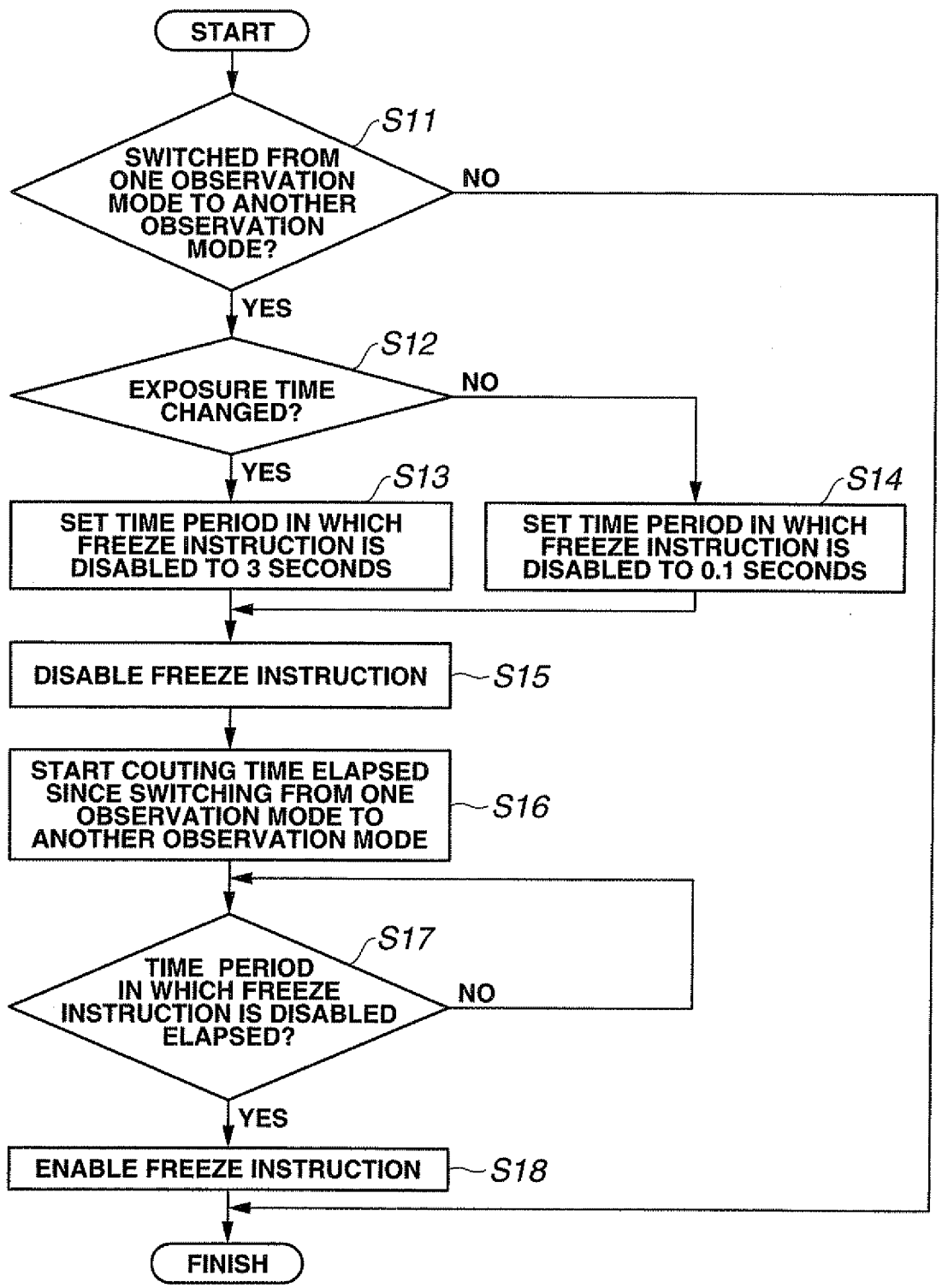
FIG. 48 is a flowchart showing an example, which differs from that of FIG. 45, of processing performed at the processor when the observation mode of the endoscope apparatus is switched from one observation mode to another observation mode according to the fifth embodiment of the present invention.

More specifically, in the processing represented by step S11 in FIG. 48, when the color shift detecting circuit 247 detects via the control circuit 240 that switching has been performed from one observation mode to another observation mode, the color shift detecting circuit 247 judges whether the exposure time has been changed in the processing represented by step S12 in FIG. 48. In other words, in the processing represented by step S12 in FIG. 48, the color shift detecting circuit 247 judges that the exposure time has been changed when detecting that the observation mode of the endoscope apparatus 201 has been switched from the normal observation mode to the fluorescence observation mode or from the fluorescence observation mode to the normal observation mode.

Then, in the processing represented by step S13 in FIG. 48, when the color shift detecting circuit 247 detects that the exposure time has been changed, the color shift detecting circuit 247 sets the time period in which the freeze instruction is disabled to three seconds. In addition, in the processing represented by step S14 in FIG. 48, when the color shift detecting circuit 247 detects that the exposure time has not been changed, the color shift detecting circuit 247 sets the time period in which the freeze instruction is disabled to 0.1 seconds.

The color shift detecting circuit 247 disables the freeze instruction in the processing represented by step S15 in FIG. 48, and in the processing represented by step S16 in FIG. 48, commences counting of the time elapsed since the switching from one observation mode to another observation mode was performed.

Subsequently, when the color shift detecting circuit 247 detects that the time period in which the freeze instruction is disabled has elapsed in the processing represented by step S17 in FIG. 48, the color shift detecting circuit 247 enables the freeze instruction in the processing represented by step S18 in FIG. 48.

In addition, for the pre-freeze processing performed at the color shift detecting circuit 247, a processing level value may be set as, for example, setting values of 1 to 7 that are indicated as "freeze levels" in a setting screen of the processor 206 shown in FIG. 47.

For example, when the processing level value is set to 1 and a freeze instruction is issued at the timing F2 shown in FIG. 46, the color shift detecting circuit 247 detects an image pickup signal having the fewest color shifts among the image pickup signals written into the memory section 239 between the time series numbers 16 to 20, and then performs pre-freeze processing so as to cause a still image based on the image pickup signal to be displayed as a freeze image on the monitor 207.

In addition, for example, when the processing level value is set to 2 and a freeze instruction is issued at the timing F2 shown in FIG. 46, the color shift detecting circuit 247 detects an image pickup signal having the fewest color shifts among the image pickup signals written into the memory section 239 between the time series numbers 13 to 20, and then performs pre-freeze processing so as to cause a still image based on the image pickup signal to be displayed as a freeze image on the monitor 207.

Furthermore, for example, when the processing level value is set to 3 and a freeze instruction is issued at the timing F2 shown in FIG. 46, the color shift detecting circuit 247 detects an image pickup signal having the fewest color shifts among the image pickup signals written into the memory section 239 between the time series numbers 10 to 20, and then performs pre-freeze processing so as to cause a still image based on the image pickup signal to be displayed as a freeze image on the monitor 207.

As seen, the color shift detecting circuit 247 performs pre-freeze processing while increasing and decreasing the time period in which a target image pickup signal among image pickup signals written into the memory section 239 is written according to a set processing level value. Moreover, the color shift detecting circuit 247 may be arranged to perform processing that increases and decreases the time period in which the freeze instruction is disabled according to a processing level value set as described above.

In addition, for example, the color shift detecting circuit 247 may be configured so as to preset the time period in which the freeze instruction is disabled to a predetermined time period during and immediately after switching from one observation mode to another observation mode is performed such as the time period between the time series numbers 5 to 14 shown in FIG. 46 and, at the same time, to determine a processing level of pre-freeze processing at the timing at which the freeze instruction is issued.

Figure 49:
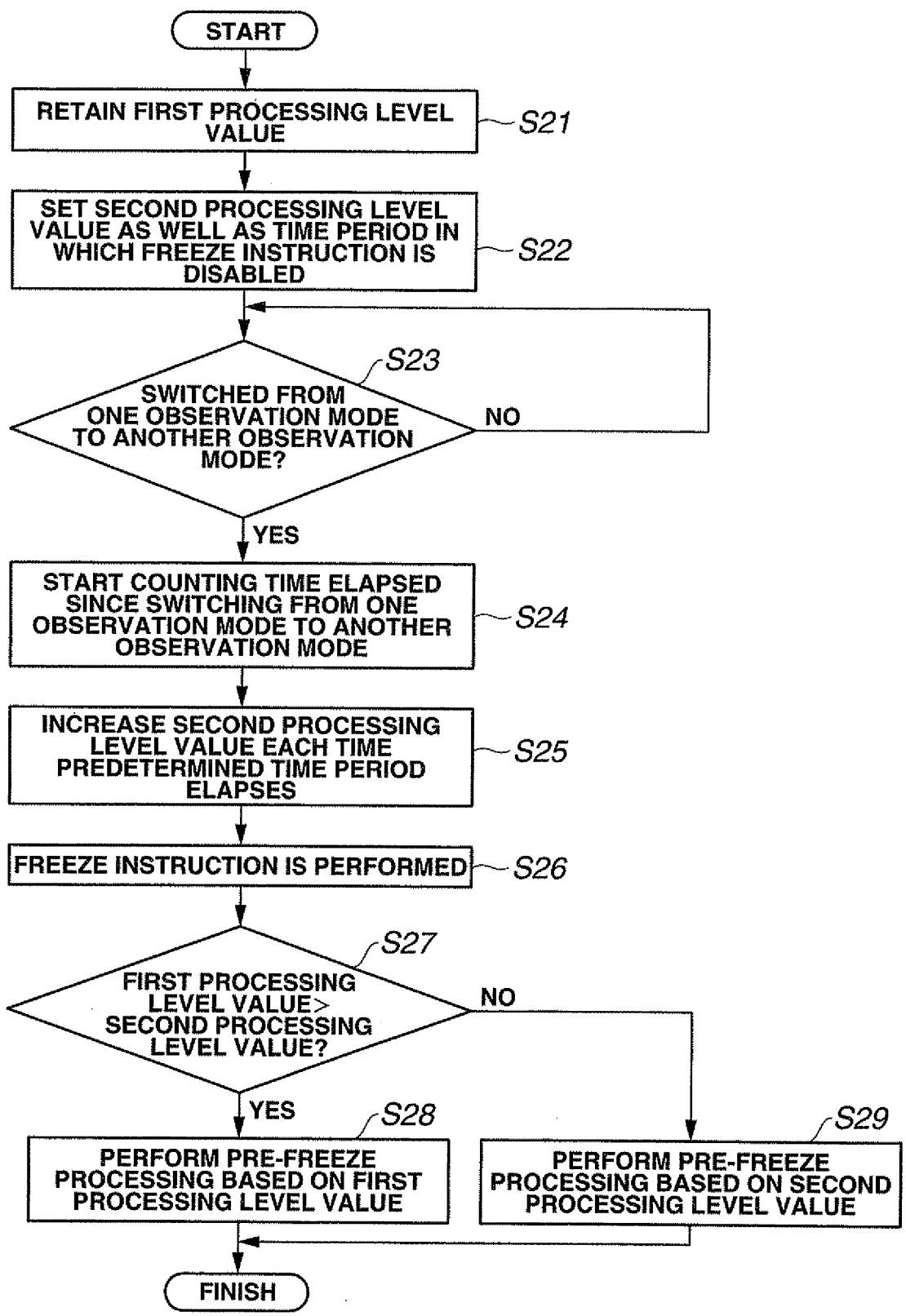
FIG. 49 is a flowchart showing an example of pre-freeze processing performed by the processor included in the endoscope apparatus according to the fifth embodiment of the present invention.

More specifically, in the processing represented by step S21 in FIG. 49, the color shift detecting circuit 247 retains a first processing level value of pre-freeze processing set by the operator or the like. Then, in the processing represented by step S22 in FIG. 49, the color shift detecting circuit 247 sets a second processing level value as an initial value of a temporary pre-freeze level value and, at the same time, sets a predetermined time period during and immediately after switching from one observation mode to another observation mode is performed as the time period in which the freeze instruction is disabled.

Subsequently, in the processing represented by step S23 in FIG. 49, when the color shift detecting circuit 247 detects via the control circuit 240 that switching has been performed from one observation mode to another observation mode, in the processing represented by step S24 in FIG. 49, the color shift detecting circuit 247 commences counting of the time elapsed since the switching from one observation mode to the other observation mode was performed. Furthermore, in the processing represented by step S25 in FIG. 49, the color shift detecting circuit 247 increases the second processing level value every time a predetermined time period (e.g., 0.1 seconds) lapses since the switching from one observation mode to the other observation mode was performed.

In the processing represented by step S26 in FIG. 49, when the color shift detecting circuit 247 detects that a freeze instruction was issued, in the processing represented by step S27 in FIG. 49, the color shift detecting circuit 247 performs a comparison between the first processing level value and the second processing level value that is the timing at which the freeze instruction was issued. Then, when the color shift detecting circuit 247 detects that the first processing level value is greater than the second processing level value, in the processing represented by step S28 in FIG. 49, the color shift detecting circuit 247 performs pre-freeze processing based on the first processing level value. In addition, when the color shift detecting circuit 247 detects that the first processing level value is equal to or below the second processing level value, in the processing represented by step S29 in FIG. 49, the color shift detecting circuit 247 performs pre-freeze processing based on the second processing level value.

As described above, the endoscope apparatus 201 according to the present embodiment capable of outputting a still image suitable for storing when switching from one observation mode to another observation mode is being performed.

The present invention is not limited to the respective embodiments described above, and various changes and modifications may be made without altering the scope thereof.

The invention claimed is:

1. An endoscope apparatus comprising:
   an endoscope including normal light image pickup means having an electronic shutter and which picks up a subject image under normal light and fluorescence image pickup means that picks up a fluorescence image from a subject; and
   an image processing apparatus that performs signal processing on image pickup signals from the normal light image pickup means and the fluorescence image pickup means to create a normal light image and a fluorescence image,
   wherein an objective optical system is provided on a front face of the fluorescence image pickup means, the objective optical system including a splitter that bisects reflected light from the subject, and two fluorescence transmitting filters having mutually different filter characteristics, the filters being arranged for each half region of an image pickup plane of the fluorescence image pickup means and transmitting light split by the splitter,
   wherein an illumination system and additionally an illumination system of a separate system are provided, the illumination system outputting a common illumination light including an excitation light having a wavelength in which the subject emits fluorescence for the normal light image pickup means and the fluorescence image pickup means, the illumination system of the separate system outputting an excitation light through a light path of a separate system in accordance with an output timing of the excitation light of the common illumination light,
   wherein the image processing apparatus includes:
      normal light image pickup control means that drives the normal light image pickup means;
      fluorescence image pickup control means that drives the fluorescence image pickup means;
      normal light image signal processing means that performs signal processing on an image pickup signal from the normal light image pickup means to create a normal light image; and
      fluorescence image signal processing means that performs signal processing on an image pickup signal including a fluorescence image of the subject to create a fluorescence image,
   wherein the normal light image pickup control means and the fluorescence image pickup control means are simultaneously driven, and
   wherein the normal light image signal processing means creates a normal light image under a reflected light from the subject caused by the common illumination light without the reflected light passing through the splitter, and simultaneously, the fluorescence image signal processing means creates two fluorescence images under light obtained by splitting, by the splitter, the reflected light from the subject caused by the excitation light of the common illumination light and the excitation light from the light path of the separate system, and transmitted through the two fluorescence transmitting filters.

2. The endoscope apparatus according to claim 1, wherein the normal light image pickup control means controls an exposure amount of the normal light image pickup means via the electronic shutter to change brightness of the normal light image to an appropriate brightness.

3. The endoscope apparatus according to claim 1, wherein the fluorescence image pickup control means controls a gain of the fluorescence image pickup means to change brightness of the fluorescence image to an appropriate brightness.

4. The endoscope apparatus according to claim 1, wherein the objective optical system further comprises two lenses that passes the light split by the splitter, the two lenses forming two fluorescence images on the image pickup plane of the fluorescence image pickup means.

\* \* \* \* \*